(12) United States Patent
Kondo et al.

(10) Patent No.: US 9,063,078 B2
(45) Date of Patent: Jun. 23, 2015

(54) METHOD AND APPARATUS FOR MEASURING CHARACTERISTICS OF OBJECT

(75) Inventors: Takashi Kondo, Nagaokakyo (JP); Kazuhiro Takigawa, Nagaokakyo (JP); Seiji Kamba, Nagaokakyo (JP); Ryoichi Fukasawa, Ohtawara (JP); Tomofumi Ikari, Ohtawara (JP)

(73) Assignee: MURATA MANUFACTURING CO., LTD, Nagaokakyo-Shi, Kyoto-Fu (JP)

( * ) Notice: Subject to any disclaimer, the term of this patent is extended or adjusted under 35 U.S.C. 154(b) by 589 days.

(21) Appl. No.: 13/530,188

(22) Filed: Jun. 22, 2012

(65) Prior Publication Data

US 2012/0262190 A1   Oct. 18, 2012

Related U.S. Application Data

(63) Continuation of application No. PCT/JP2010/071988, filed on Dec. 8, 2010.

(30) Foreign Application Priority Data

Dec. 22, 2009 (JP) ................................ 2009-290741
Jun. 18, 2010 (JP) ................................ 2010-139347

(51) Int. Cl.
*G01N 22/00* (2006.01)
*G01N 21/3581* (2014.01)
(Continued)

(52) U.S. Cl.
CPC ............ *G01N 21/3581* (2013.01); *G01N 22/00* (2013.01); *G01N 22/04* (2013.01); *G01N 22/02* (2013.01); *G01N 2021/0339* (2013.01); *G01N 21/3563* (2013.01)

(58) Field of Classification Search
CPC .......... G01N 21/3581; G01N 21/3563; G01N 22/00; G01N 22/02; G01N 22/04; G01N 27/20; G01N 27/24; G01N 27/61; G01N 27/82; G01N 2021/0339; G01R 31/026
USPC ......... 324/639, 637, 629, 600, 642, 713, 718, 324/555, 240, 238, 237, 216, 456; 250/341.1
See application file for complete search history.

(56) References Cited

U.S. PATENT DOCUMENTS 3,829,764 A * 8/1974 Bosisio ......................... 324/632
(Continued)

FOREIGN PATENT DOCUMENTS

JP   2006-133013 A   5/2006
JP   2007-010366 A   1/2007
(Continued)

OTHER PUBLICATIONS

PCT/2010/071988 Written Opinion dated Jan. 7, 2009.

*Primary Examiner* — Hoai-An D Nguyen
(74) *Attorney, Agent, or Firm* — Arent Fox LLP

(57) ABSTRACT

A measuring method for measuring characteristics of an object to be measured, the measuring method including holding the object on a void-arranged structure having at least two void portions that pass therethrough in a direction perpendicular to a principal surface thereof, and applying electromagnetic waves to the void-arranged structure on which the object is held to detect frequency characteristics of the electromagnetic waves transmitted through the void-arranged structure. The void-arranged structure has a grid structure in which the void portions are periodically arranged in at least one direction on the principal surface of the void-arranged structure. The characteristics of the object are measured on the basis of a relationship between a first frequency characteristic and a second frequency characteristic.

20 Claims, 24 Drawing Sheets

(51) Int. Cl.
  *G01N 22/04* (2006.01)
  *G01N 22/02* (2006.01)
  *G01N 21/03* (2006.01)
  *G01N 21/3563* (2014.01)

(56) References Cited

U.S. PATENT DOCUMENTS

| | | | | |
|---|---|---|---|---|
| 5,146,171 | A | * | 9/1992 | Bradley .................... 324/639 |
| 5,331,284 | A | * | 7/1994 | Jean et al. ................. 324/639 |
| 5,455,516 | A | * | 10/1995 | Jean et al. ................. 324/639 |
| 7,982,469 | B2 | * | 7/2011 | Jakkula et al. ............. 324/633 |
| 8,400,166 | B2 | * | 3/2013 | Geren ....................... 324/637 |
| 2010/0025586 | A1 | * | 2/2010 | Ogawa et al. .............. 250/341.1 |
| 2012/0126123 | A1 | * | 5/2012 | Kondo et al. .............. 250/341.1 |
| 2012/0137755 | A1 | * | 6/2012 | Takigawa et al. ........... 73/61.49 |
| 2012/0153159 | A1 | * | 6/2012 | Kamba et al. .............. 250/341.3 |

FOREIGN PATENT DOCUMENTS

| | | |
|---|---|---|
| JP | 2007-147314 A | 6/2007 |
| JP | 2007-163181 A | 6/2007 |
| JP | 2008-185552 A | 8/2008 |

* cited by examiner

METHOD AND APPARATUS FOR MEASURING CHARACTERISTICS OF OBJECT

CROSS REFERENCE TO RELATED APPLICATIONS

The present application is a continuation of International application No. PCT/JP2010/071988, filed Dec. 8, 2010, which claims priority to Japanese Patent Application No. 2009-290741, filed Dec. 22, 2009, and Japanese Patent Application No. 2010-139347, filed Jun. 18, 2010, the entire contents of each of which are incorporated herein by reference.

FIELD OF THE INVENTION

The present invention relates to a method for measuring characteristics of an object to be measured (hereinafter may be referred to as "object"), the method including holding the object on a void-arranged structure, applying electromagnetic waves to the void-arranged structure on which the object is held, and detecting the electromagnetic waves transmitted through the void-arranged structure to measure the characteristics of the object. The present invention also relates to a measuring apparatus used in carrying out the method.

BACKGROUND OF THE INVENTION

Conventionally, a measuring method has been used which includes, for analyzing material characteristics, holding an object on a void-arranged structure, applying electromagnetic waves to the void-arranged structure on which the object is held, and analyzing the resulting transmittance spectra to measure characteristics of the object. Specifically, for example, terahertz waves are applied to a metal mesh having an object (e.g., protein) deposited thereon to analyze the resulting transmittance spectra.

Japanese Unexamined Patent Application Publication No. 2007-010366 (Patent Literature (PTL) 1) and Japanese Unexamined Patent Application Publication No. 2007-163181 (PTL 2) each disclose a method which includes a void-arranged structure having void regions (e.g., metal mesh), an object on the void-arranged structure, an electromagnetic-wave emitting unit configured to emit electromagnetic waves toward the object, and a detecting unit configured to measure the electromagnetic waves transmitted through the void-arranged structure. This method measures characteristics of the object on the basis of the fact that a frequency characteristic is changed by the presence of the object.

Japanese Unexamined Patent Application Publication No. 2008-185552 (PTL 3) discloses a method in which electromagnetic waves emitted from an electromagnetic-wave emitting unit toward a void-arranged structure are incident at an angle on a flat surface containing void regions, and characteristics of an object are measured by focusing on a frequency shift of a dip waveform appearing in a frequency characteristic of a measured value.

The methods for measuring characteristics of an object disclosed in PTL 1 to PTL 3 involve measuring not only a frequency characteristic obtained when the object is present, but also measuring, as a reference, a frequency characteristic obtained when no object is present (i.e., when a void-arranged structure alone is provided) (e.g., see FIG. 9 in PTL 3). These methods may further involve measuring a frequency characteristic obtained when no void-arranged structure is provided (i.e., measuring a frequency characteristic of a background). This means that in these methods, characteristics of an object are measured as the amount of change from a reference value.

PTL 1: Japanese Unexamined Patent Application Publication No. 2007-010366
PTL 2: Japanese Unexamined Patent Application Publication No. 2007-163181
PTL 3: Japanese Unexamined Patent Application Publication No. 2008-185552

SUMMARY OF THE INVENTION

In such conventional measuring methods, since a change in frequency characteristic decreases with a decreasing quantity of an object, variation in frequency characteristic of a void-arranged structure serving as a reference (e.g., dimensional variation of a metal mesh) may cause a significant error.

Generally, to obtain a frequency characteristic of sample A, it is necessary to measure, as a reference, a frequency characteristic of a void-arranged structure in advance. This increases the number of times of measurement. Moreover, it takes time to calibrate a measured value of an object using the measured frequency characteristic of the void-arranged structure. Additionally, as the overall time of measurement operation increases, the effect of temporal changes in measurement environment increases. This may lead to a significant error in the obtained result.

The prevent invention aims to provide a measuring method in which characteristics of an object can be measured with high measurement sensitivity and high reproducibility even when the quantity of the object is very small, and also to provide a measuring apparatus used in carrying out the measuring method.

(1) A measuring method for measuring characteristics of an object to be measured includes holding the object on a void-arranged structure having at least two void portions that pass therethrough in a direction perpendicular to a principal surface thereof, and applying electromagnetic waves to the void-arranged structure on which the object is held to detect frequency characteristics of the electromagnetic waves transmitted through the void-arranged structure. The void-arranged structure has a grid structure in which the void portions are periodically arranged in at least one direction on the principal surface of the void-arranged structure. A first frequency characteristic and a second frequency characteristic are detected as the frequency characteristics. A dip waveform appears in the first frequency characteristic. No dip waveform or a dip waveform having a depth smaller than that of the dip waveform in the first frequency characteristic appears in the second frequency characteristic. The characteristics of the object are measured on the basis of a relationship between the first frequency characteristic and the second frequency characteristic.

(2) In the measuring method according to (1), the characteristics of the object are measured using a difference spectrum S determined from the first frequency characteristic and the second frequency characteristic by the following equation (1):

[Numerical Expression 1]

$$S = \frac{aTx + bTy}{cTx + dTy} \quad (1)$$

where Ty is a transmittance of an electromagnetic wave in the first frequency characteristic, Tx is a transmittance of an electromagnetic wave in the second frequency characteristic, and a, b, c, and d are independent constants.

(3) In the measuring method according to (2), the quantity of the object is calculated by comparing a specific peak value of the difference spectrum S with a calibration curve generated on the basis of specific peak values of difference spectra S obtained by measuring various quantities of the object.

(4) In the measuring method according to (1), the dip waveform appearing in the first frequency characteristic is generated by TE11-mode-like resonance of the void-arranged structure.

(5) In the measuring method according to (1), the electromagnetic waves are linearly polarized electromagnetic waves. When the principal surface of the void-arranged structure is not parallel to the polarization direction of the electromagnetic waves, a frequency characteristic of an electromagnetic wave transmitted through the void-arranged structure is detected as the first frequency characteristic. When the principal surface of the void-arranged structure is parallel to the polarization direction of the electromagnetic waves, a frequency characteristic of an electromagnetic wave transmitted through the void-arranged structure is detected as the second frequency characteristic.

(6) In the measuring method according to (1), a first electromagnetic wave and a second electromagnetic wave, which are linearly polarized electromagnetic waves, are applied to the void-arranged structure such that polarization directions thereof are different from each other. A frequency characteristic of the first electromagnetic wave transmitted through the void-arranged structure is detected as the first frequency characteristic, and a frequency characteristic of the second electromagnetic wave transmitted through the void-arranged structure is detected as the second frequency characteristic.

(7) In the measuring method according to (6), the first electromagnetic wave and the second electromagnetic wave are applied to the void-arranged structure such that a propagation direction of the first electromagnetic wave is the same as that of the second electromagnetic wave, a polarization direction of the first electromagnetic wave is one direction perpendicular to the propagation direction, and a polarization direction of the second electromagnetic wave is perpendicular to both the propagation direction and the polarization direction of the first electromagnetic wave.

(8) In the measuring method according to (7), the void-arranged structure is formed by a periodic array of the void portions arranged in rows and columns in a square grid pattern. The void-arranged structure is placed such that when being projected onto a plane perpendicular to the propagation direction, one of the row and column directions of the void portions coincides with the polarization direction of the first electromagnetic wave, and the other of the row and column directions coincides with the polarization direction of the second electromagnetic wave.

(9) In the measuring method according to (7), the void-arranged structure is placed by being rotated from a position at which the principal surface thereof is perpendicular to the propagation direction by a given angle about a rotation axis passing through the center of gravity of the void-arranged structure and parallel to the polarization direction of the second electromagnetic wave.

(10) In the measuring method according to (1), a frequency characteristic of the void-arranged structure obtained in the case of applying an electromagnetic wave to the void-arranged structure in a predetermined first direction with respect to the principal surface of the void-arranged structure is detected as the first frequency characteristic, and a frequency characteristic of the void-arranged structure obtained in the case of applying an electromagnetic wave to the void-arranged structure in a second direction different from the first direction with respect to the principal surface of the void-arranged structure is detected as the second frequency characteristic.

(11) In the measuring method according to (10), the second direction is perpendicular to the principal surface of the void-arranged structure.

(12) In the measuring method according to (10), the electromagnetic wave applied in the first direction and the electromagnetic wave applied in the second direction are linearly polarized electromagnetic waves.

(13) In the measuring method according to (12), the void-arranged structure is formed by a periodic array of the void portions arranged in rows and columns in a square grid pattern. In the case of detecting the first frequency characteristic, the void-arranged structure is placed by being rotated from a position where the principal surface thereof is perpendicular to the propagation direction of the electromagnetic wave by a predetermined angle about a predetermined rotation axis not parallel to the polarization direction of the electromagnetic wave, such that when the void-arranged structure is projected onto a plane perpendicular to the propagation direction of the electromagnetic wave, one of the row and column directions of the void portions coincides with the polarization direction of the electromagnetic wave.

(14) A measuring apparatus is used in carrying out the measuring method according to (7).

(15) The measuring apparatus according to (14) includes an electromagnetic-wave emitting unit for applying the first electromagnetic wave and the second electromagnetic wave having different polarization directions to the void-arranged structure.

(16) In the measuring apparatus according to (14), the electromagnetic-wave emitting unit includes a polarization modulator capable of modulating a polarization state of the linearly polarized electromagnetic waves to two different polarization states for application of the first electromagnetic wave and the second electromagnetic wave.

(17) A measuring apparatus is used in carrying out the measuring method according to (11).

(18) The measuring apparatus according to (17) includes a position control mechanism capable of controlling a position of the void-arranged structure.

(19) In the measuring apparatus according to (18), the position control mechanism has a rotating function.

(20) The measuring apparatus according to (17) includes an electromagnetic-wave emitting unit for applying electromagnetic waves to the void-arranged structure on which the object is held, and a branching filter capable of separating the electromagnetic waves emitted from the electromagnetic-wave emitting unit into a first electromagnetic wave for obtaining the first frequency characteristic and a second electromagnetic wave for obtaining the second frequency characteristic.

(21) The measuring apparatus according to (17) includes a plurality of light sources and/or a plurality of detectors.

In the measuring method of the present invention, it is possible to eliminate or reduce the effect of variation in frequency characteristic obtained when no object is present, such as variation in frequency characteristic of a void-arranged structure (e.g., dimensional variation among void-arranged structures). Thus, even when the quantity of an object is very small, characteristics of the object can be measured with high measurement sensitivity and high reproducibility.

Additionally, since there is no need to measure, as a reference, a frequency characteristic of a void-arranged structure obtained when no object is present, it is possible to reduce the number of times of measurement and simplify the operation of calibrating the measured value. Since this simplifies the measurement operation and reduces the length of time required for the measurement, the effect of an error caused by temporal changes in measurement environment can be reduced.

BRIEF DESCRIPTION OF THE DRAWINGS

FIG. 4(a) illustrates the case of applying a first electromagnetic wave, and FIG. 4(b) illustrates the case of applying a second electromagnetic wave.

FIG. 5(a) illustrates the case of applying a first electromagnetic wave, and FIG. 5(b) illustrates the case of applying a second electromagnetic wave.

DETAILED DESCRIPTION OF THE PREFERRED EMBODIMENTS

The present invention relates to a measuring method for measuring characteristics of an object to be measured, the measuring method including holding the object on a void-arranged structure having at least two void portions that pass therethrough in a direction perpendicular to a principal surface thereof, and applying electromagnetic waves to the void-arranged structure on which the object is held to detect frequency characteristics of the electromagnetic waves transmitted through the void-arranged structure.

Electromagnetic waves used in the measuring method of the present invention are not particularly limited, but are preferably terahertz waves in the frequency range of 20 GHz to 120 THz. Specifically, for example, the electromagnetic waves may be terahertz waves generated from a short-optical pulse laser, which serves as a light source, by the optical rectification effect of electro-optical crystal, such as ZnTe. Another example is terahertz waves generated from a short-optical pulse laser, which serves as a light source, by exciting free electrons in a photoconductive antenna and applying a voltage to the photoconductive antenna to instantaneously generate a current. Still another example is terahertz waves generated from a high-pressure mercury lamp or high-temperature ceramic.

Figure 1:
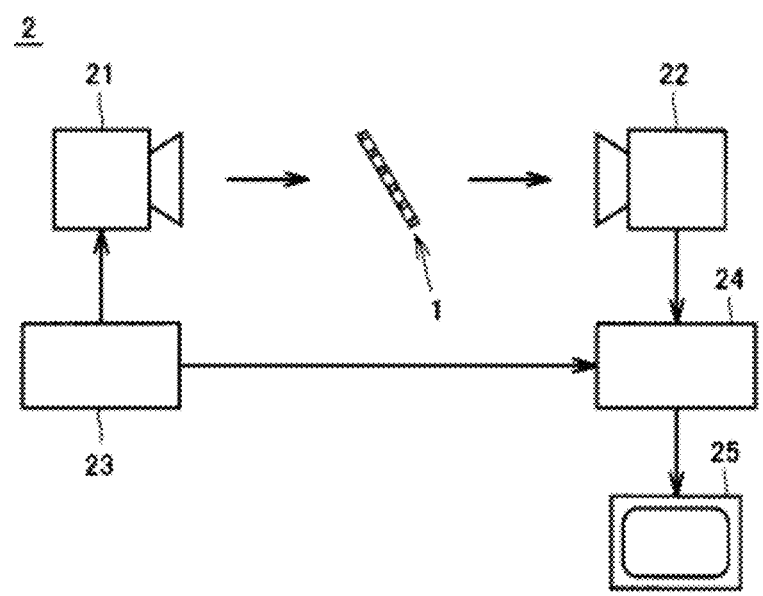
FIG. 1 is a schematic diagram for explaining an outline of a measuring method according to the present invention.

An outline of a measuring method according to the present invention will be described with reference to FIG. 1. FIG. 1 is a diagram schematically illustrating an overall configuration of a measuring apparatus 2 used in the measuring method of the present invention, and the placement of a void-arranged structure 1 in the measuring apparatus 2. As illustrated in FIG. 1, the measuring apparatus 2 includes an electromagnetic-wave emitting unit 21 that generates and emits electromagnetic waves, and a detecting unit 22 that detects the electromagnetic waves transmitted through the void-arranged structure 1. The measuring apparatus 2 also includes an emission control unit 23 that controls the operation of the electromagnetic-wave emitting unit 21, an analysis processing unit 24 that analyzes a result of detection performed by the detecting unit 22, and a display unit 25 that displays a result of analysis performed by the analysis processing unit 24. For the purpose of synchronous detection, the emission control unit 23 may be connected to the analysis processing unit 24.

In the measuring apparatus 2 described above, the electromagnetic-wave emitting unit 21 generates and emits electromagnetic waves under control of the emission control unit 23. The electromagnetic waves emitted from the electromagnetic-wave emitting unit 21 are applied to the void-arranged structure 1, scattered by the void-arranged structure 1, and detected by the detecting unit 22. The electromagnetic waves detected by the detecting unit 22 are transferred as electrical signals to the analysis processing unit 24 and displayed, for example, as transmittance frequency characteristics (transmittance spectra) in a visible form in the display unit 25.

The void-arranged structure used in the present invention is a structure in which at least two void portions that pass therethrough in a direction perpendicular to a principal surface thereof are periodically arranged in at least one direction on the principal surface. The void portions do not necessarily have to be periodically arranged over the entire void-arranged structure. It is only necessary that the void portions be periodically arranged in at least part of the void-arranged structure. The void-arranged structure is preferably a quasi-periodic structure or periodic structure. A quasi-periodic structure is a structure which does not have a translational symmetry, but maintains orderly arrangement. Examples of the quasi-periodic structure include a Fibonacci structure (one-dimensional quasi-periodic structure) and a Penrose structure (two-dimensional quasi-periodic structure). A periodic structure is a structure which has a spatial symmetry, typified by a translational symmetry. Periodic structures are classified into a one-dimensional periodic structure, a two-dimensional periodic structure, and a three-dimensional periodic structure, in accordance with dimensions of their symmetries. Examples of the one-dimensional periodic structure include a wire grid structure and a one-dimensional diffraction grating. Examples of the two-dimensional periodic structure include a mesh filter and a two-dimensional diffraction grating. Of the periodic structures described above, a two-dimensional periodic structure is preferably used. More preferably, a two-dimensional periodic structure having void portions regularly arranged in rows and columns (in a quadrilateral array) is used.

Figure 2A:
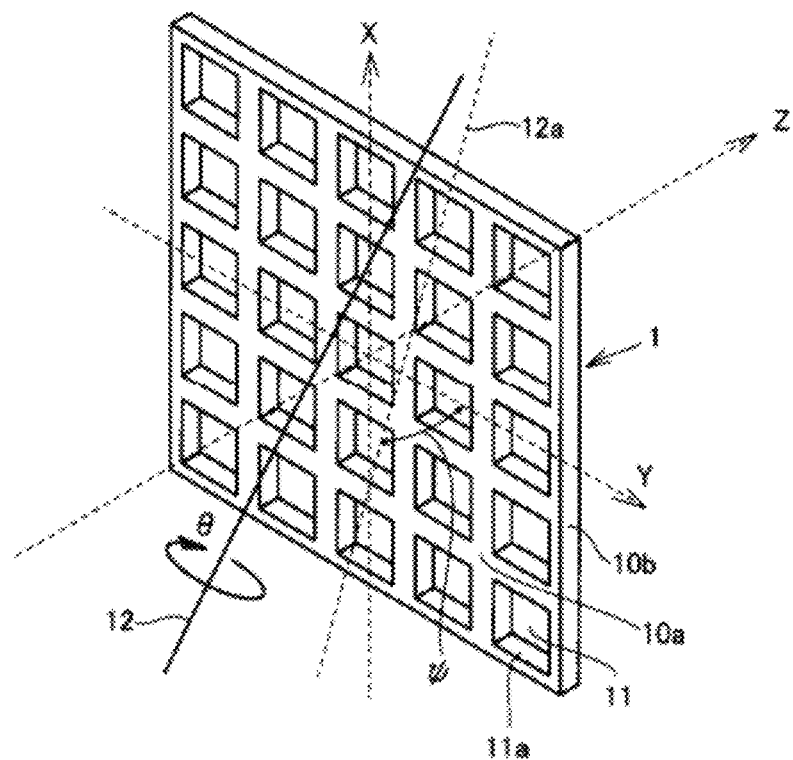
FIG. 2(a) is a perspective view of a void-arranged structure used in the present invention.
Figure 2B:
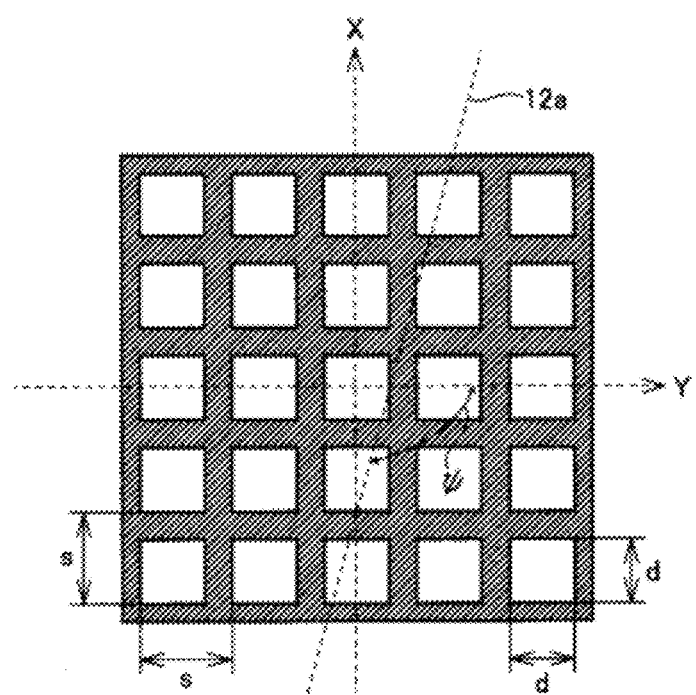
FIG. 2(b) is a schematic diagram for explaining a grid structure of the void-arranged structure.

Examples of the two-dimensional periodic structure having a quadrilateral array of void portions include a plate-like structure (grid structure) in which void portions are arranged in a matrix at regular intervals as illustrated in FIG. 2(a) and FIG. 2(b). The void-arranged structure 1 illustrated in FIG. 2(a) is a plate-like structure in which square void portions 11, as viewed from a principal surface 10a, are evenly spaced in two directions (row and column directions in FIG. 2(b)) parallel to the sides of the square. The void portions are not limited to be square, but may be rectangular, circular, or elliptical. As long as the void portions are arranged in a quadrilateral array, spacings in the two directions of arrangement do not have to be equal. For example, the void portions may be arranged in a rectangular array.

The shape and dimensions of void portions of a void-arranged structure are appropriately designed, for example, in accordance with the measuring method, material properties of the void-arranged structure, and the frequencies of electromagnetic waves used, and thus are difficult to generalize their ranges. For detection of forward-scattered electromagnetic waves, it is preferable, in the void-arranged structure 1 illustrated in FIG. 2(a), that a grid spacing between adjacent void portions indicated by "s" in FIG. 2(b) be greater than or equal to 1/10 and less than or equal to 10 times the wavelength of the electromagnetic waves used in the measurement. If the grid spacing "s" between adjacent void portions falls outside this range, the occurrence of scattering may be hindered. As for an opening size of each void portion, it is preferable that an opening size indicated by "d" in FIG. 2(b) be greater than or equal to 1/10 and less than or equal to 10 times the wavelength of the electromagnetic waves used in the measurement. If the opening size of each void portion falls outside this range, the intensity of the forward-scattered electromagnetic waves may be weakened and it may be difficult to detect signals.

The thickness of a void-arranged structure is appropriately designed, for example, in accordance with the measuring method, material properties of the void-arranged structure, and the frequencies of electromagnetic waves used, and thus is difficult to generalize its range. For detection of forward-scattered electromagnetic waves, it is preferable that the thickness of the void-arranged structure be less than or equal to several times the wavelength of the electromagnetic waves used in the measurement. If the thickness of the void-arranged structure exceeds this range, the intensity of the forward-scattered electromagnetic waves may be weakened and it may be difficult to detect signals.

The measuring method of the present invention is characterized in that a measuring method, such as that described above, detects a plurality of frequency characteristics (first frequency characteristic and second frequency characteristic). In the first frequency characteristic, a dip waveform appears. In the second frequency characteristic, no dip waveform or a dip waveform having a depth smaller than that of the dip waveform in the first frequency characteristic appears. It is preferable that virtually no dip waveform appear in the second frequency characteristic. Even when a dip waveform appears in the second frequency characteristic, it is preferable that the depth of the dip waveform be one or more points smaller than that of the dip waveform in the first frequency characteristic.

Here, a dip waveform is a waveform of a valley portion (downwardly protruding portion) that appears in part of a frequency characteristic (e.g., transmittance spectrum) of a structure which involves scattering, in a frequency range where the ratio of a detected electromagnetic wave to an applied electromagnetic wave (e.g., transmittance of an electromagnetic wave) is relatively large.

Figure 41:
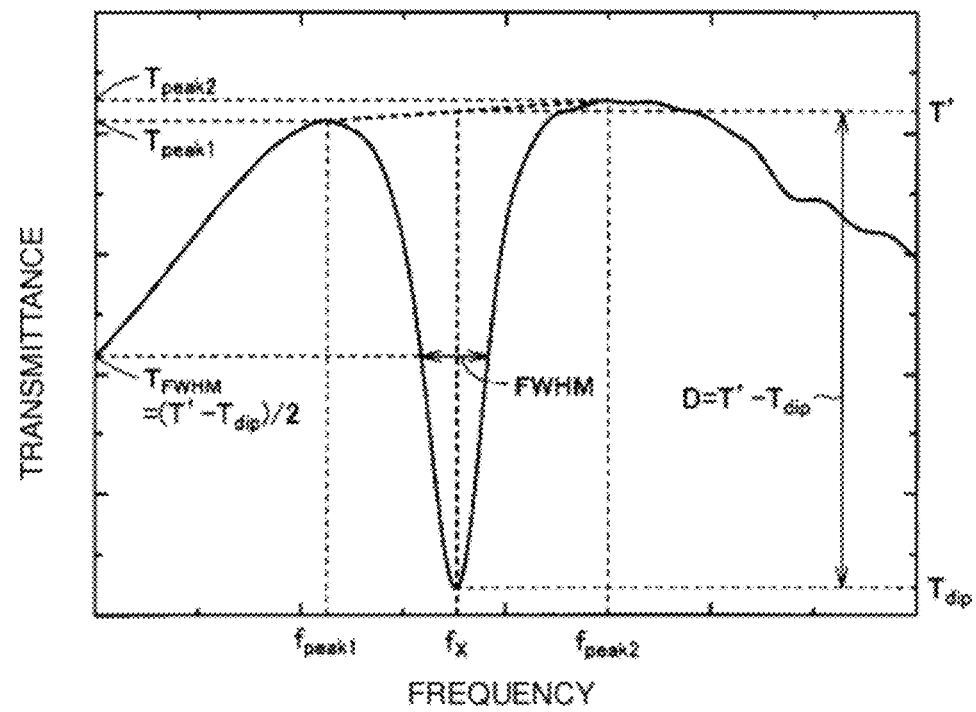
FIG. 41 is a graph for explaining a depth of a dip waveform defined in the present invention.

A depth (D) of a dip waveform will be defined with reference to FIG. 41. A transmittance (maximum value) at a frequency $f_{peak1}$ of a peak on the lower-frequency side of a dip is represented by $T_{peak1}$ a transmittance (maximum value) at a frequency $f_{peak2}$ of a peak on the higher-frequency side of the dip is represented by $T_{peak2}$ and a transmittance (minimum value) at a frequency fx of the dip is represented by $T_{dip}$. A point of intersection of fx and a straight line which connects $T_{peak1}$ and $T_{peak2}$ is represented by T'. A difference between T' and $T_{dip}$, [T'−$T_{dip}$], is defined as the depth (D) of the dip waveform.

A dip waveform can be generated by breaking a spatial symmetry with respect to an electromagnetic wave incident on a void-arranged structure. For example, a dip waveform can be generated when a principal surface of the void-arranged structure is displaced (or tilted) from a position perpendicular to the propagation direction of an incident electromagnetic wave. A dip wavefm can also be generated when void portions of the void-arranged structure are formed not to be reflection-symmetric with respect to a virtual surface orthogonal to the polarization direction of an electromagnetic wave applied to the void-arranged structure. A dip waveform can also be generated when the void-arranged structure is placed such that the shape of an array of void portions of the void-arranged structure does not have a spatial symmetry.

A dip waveform in the first frequency characteristic is preferably generated by TE11-mode-like resonance of the void-arranged structure (where each void portion serves as a waveguide). Alternatively, a dip waveform in the first frequency characteristic is preferably generated by a reduction in TE10-mode-like resonance of the void-arranged structure (where each void portion serves as a waveguide). This is because the dip waveform appearing in the first frequency characteristic is sharpened, and sensitivity for measuring an object is improved.

A dip waveform is generated in the first frequency characteristic by TE11-mode-like resonance (or a reduction in TE10-mode-like resonance) of the void-arranged structure when, for example, the void-arranged structure is placed such that its principal surface is not parallel to the polarization direction of a first electromagnetic wave. In other words, the void-arranged structure is placed by being rotated from a position at which its principal surface is perpendicular to the propagation direction of the first electromagnetic wave by a given angle about a predetermined rotation axis not parallel to the polarization direction of the first electromagnetic wave.

More specifically, as described below, when the first electromagnetic wave and a second electromagnetic wave propagate in the same direction (Z-axis direction), the polarization direction of the first electromagnetic wave is one direction (Y-axis direction) perpendicular to the Z-axis direction, and the polarization direction of the second electromagnetic wave is a direction (X-axis direction) perpendicular to the Z-axis direction and the Y-axis direction, the void-arranged structure is preferably placed by being rotated from a position at which its principal surface is perpendicular to the Z-axis direction (or parallel to the X-axis direction and the Y-axis direction) by a given angle about a predetermined rotation axis (X-axis) parallel to the X-axis direction passing through the center of gravity of the void-arranged structure.

As described above, a dip waveform can be generated by TE11-mode-like resonance when the void-arranged structure is tilted with respect to the propagation direction and the polarization direction of the first electromagnetic wave. A dip waveform can also be generated by TE11-mode-like resonance when void portions of the void-arranged structure are formed not to be reflection-symmetric with respect to a virtual surface orthogonal to the plane of polarization of the first electromagnetic wave. In the latter case, a dip waveform can be generated by TE11-mode-like resonance even when the void-arranged structure is placed to be perpendicular to the propagation direction of the first electromagnetic wave.

For example, the void portions are formed such that a part of the periodic structure forming each void portion is provided with a protrusion or notch. In this case, it is preferable, in the part of the periodic structure forming the void portion, that a protrusion be provided at a position where the intensity of electric field is relatively high when TE11-mode-like resonance occurs or a notch be provided at a position where the intensity of electric field is relatively low when TE11-mode-like resonance occurs. The void portions each may be, for example, trapezoidal, convex, concave, polygonal, or star-shaped as viewed in a direction perpendicular to the principal surface of the periodic structure, and the void-arranged structure may be placed not to be reflection-symmetric with respect to a virtual surface orthogonal to the plane of polarization of the first electromagnetic wave.

To prevent a dip waveform from appearing in the second frequency characteristic, it is only necessary to select a condition other than the above-described conditions that allow a dip waveform to appear. For example, the void-arranged structure may be placed such that its principal surface is parallel to the polarization direction of the second electromagnetic wave, and it is particularly preferable that the void-arranged structure be placed such that its principal surface is perpendicular to the propagation direction of the electromagnetic waves. With this placement, it is possible to prevent a dip waveform from appearing in the second frequency characteristic by using a void-arranged structure having void portions which are formed to be reflection-symmetric with respect to a virtual surface orthogonal to both the plane of polarization of the second electromagnetic wave (i.e., plane containing the polarization direction and the propagation direction) and the principal surface of the void-arranged structure.

In the measuring method of the present invention, it is preferable that characteristics of an object be measured using a difference spectrum S determined from the first frequency characteristic and the second frequency characteristic by equation (1) described above. Measuring characteristics of an object using the difference spectrum S means, for example, measuring characteristics of an object on the basis of a change in peak value of the difference spectrum S or in frequency at which a peak of the difference spectrum S occurs, or a change in the shape of the difference spectrum.

Conventionally, a frequency characteristic of a void-arranged structure alone is measured as a reference and used in calibration. As compared to this, using the difference spectrum S can reduce the effect of variation in frequency characteristic obtained when no object is present, such as variation in frequency characteristic of the void-arranged structure, and can improve the sensitivity for measuring an object. Although its underlying principles are not known in detail, it was experimentally confirmed that using the difference spectrum S can reduce the effect of dimensional variation of the void-arranged structure on the first frequency characteristic and the second frequency characteristic.

In Example 4 described below, in a region around a dip waveform in FIG. 26, a waveform $Ty_2$ and a waveform $Tx_2$ corresponding to an opening size of 184 μm are obtained by shifting a waveform $Ty_1$ and a waveform $Tx_1$ corresponding to an opening size of 180 μm by 0.014 THz (0.028%) to the upper left. That is, when the opening size becomes larger, the peak frequency decreases and the transmittance increases. When a difference between both waveforms for each opening size is taken, changes in frequency are maintained, but changes in transmittance are cancelled out and reduced.

For measuring the quantity of an object in the present invention, it is preferable to calculate the quantity of the object by comparing a specific peak value of the difference spectrum S with a calibration curve generated on the basis of specific peak values of difference spectra S obtained by measuring various quantities of the object in advance.

Examples of a method for detecting the first frequency characteristic and the second frequency characteristic include a method in which the first electromagnetic wave and the second electromagnetic wave, which are linearly polarized electromagnetic waves, are applied to the void-arranged structure such that their polarization directions are different from each other. Then, a frequency characteristic of the first electromagnetic wave transmitted through the void-arranged structure is detected as the first frequency characteristic, and a frequency characteristic of the second electromagnetic wave transmitted through the void-arranged structure is detected as the second frequency characteristic.

The first electromagnetic wave and the second electromagnetic wave may be linearly polarized electromagnetic waves obtained after electromagnetic waves emitted from a light source, such as a non-polarized or circularly polarized light source, pass through a polarizer. Alternatively, the first electromagnetic wave and the second electromagnetic wave may be linearly polarized electromagnetic waves emitted from a polarized light source.

The first electromagnetic wave and the second electromagnetic wave may be applied in accordance with a procedure in which, after one of the first electromagnetic wave and the second electromagnetic wave is applied to detect a frequency characteristic, the other electromagnetic wave is applied to detect another frequency characteristic. For efficient measurement, it is preferable that after simultaneous application of the first electromagnetic wave and the second electromagnetic wave, frequency characteristics (first frequency characteristic and second frequency characteristic) of the respective electromagnetic waves be measured simultaneously.

The first electromagnetic wave and the second electromagnetic wave may be supplied from either different light sources or a single light source. Examples of a method for supplying the first electromagnetic wave and the second electromagnetic wave from a single light source include a method in which electromagnetic waves emitted from a single light source are converted to linearly polarized electromagnetic waves as they pass through a linear polarizer, and the polarization state of the linearly polarized electromagnetic waves is modulated into two different polarization states by a polarization modulator to form the first electromagnetic wave and the second electromagnetic wave, for example. After the polarization state of the linearly polarized electromagnetic waves is modulated into two different polarization states, the resulting electromagnetic waves are transmitted through the void-arranged structure. Then, by sweeping the electromagnetic waves with a frequency smaller than the modulation frequency, the first frequency characteristic and the second frequency characteristic can be detected.

In the method of the present invention, the first electromagnetic wave and the second electromagnetic wave are preferably applied to the void-arranged structure such that the first electromagnetic wave and the second electromagnetic wave propagate in the same direction (Z-axis direction), the polarization direction of the first electromagnetic wave is one direction (Y-axis direction) perpendicular to the Z-axis direction, and the polarization direction of the second electromagnetic wave is a direction (X-axis direction) perpendicular to the Z-axis direction and the Y-axis direction (see FIG. 2). Thus, by applying the electromagnetic waves and properly placing (as described below) the void-arranged structure having void portions periodically arranged in rows and columns in a square grid pattern, it is possible to sharpen a dip waveform appearing in the first frequency characteristic and improve sensitivity for measuring an object.

The void-arranged structure may be placed such that its principal surface is perpendicular to the propagation direction of the first electromagnetic wave and the second electromagnetic wave (Z-axis direction), or may be placed (at an angle) such that its principal surface is not perpendicular to the propagation direction of the first electromagnetic wave and the second electromagnetic wave (Z-axis direction). If the void-arranged structure is formed by a periodic array of the void portions arranged in rows and columns in a square grid pattern, the void-arranged structure is preferably placed such that when being projected onto a plane perpendicular to the Z-axis, one of the row and column directions of the void portions coincides with the X-axis direction and the other coincides with the Y-axis direction.

When the void-arranged structure is to be positioned at an angle, the void-arranged structure is placed by being rotated from a position at which its principal surface is parallel to the X-axis direction and the Y-axis direction (or perpendicular to the Z-axis direction) by a given angle about a specific rotation axis. Here, it is preferable that the void-arranged structure be placed by being rotated by a given angle about a rotation axis (X-axis) parallel to the X-axis direction passing through the center of gravity of the void-arranged structure. This is because, with this placement, it is possible to sharpen a dip waveform appearing in the first frequency characteristic and further improve sensitivity for measuring an object.

(Measuring Apparatus)

The present invention also relates to a measuring apparatus used in carrying out the measuring method described above. The void-arranged structure preferably includes an electromagnetic-wave emitting unit for applying the first electromagnetic wave and the second electromagnetic wave, which are linearly polarized electromagnetic waves, such that their polarization directions are different from each other. In this case, an interferometer may be further provided between the electromagnetic-wave emitting unit and a detector that detects electromagnetic waves transmitted through the void-arranged structure.

For applying the first electromagnetic wave and the second electromagnetic wave, the electromagnetic-wave emitting unit preferably includes a polarization modulator capable of modulating the polarization state of linearly polarized electromagnetic waves into two different polarization states.

Thus, the polarization state of linearly polarized electromagnetic waves is modulated into two different polarization states, and the resulting electromagnetic waves are swept with a frequency smaller than the modulation frequency, so that the first frequency characteristic and the second frequency characteristic are detected. It is thus possible to reduce the number of times of measurement (sweeping) and simplify the operation of calibrating the measured value. Since this simplifies the measurement operation and reduce the length of time required for the measurement, the effect of an error caused by temporal changes in measurement environment can be reduced.

In the present invention, measuring characteristics of an object refers to quantitative and various qualitative determinations of a compound, which is an object to be measured. This includes, for example, measuring the content of a small quantity of the object in a solution, and making an identification of the object. Specifically, for example, the void-arranged structure is dipped into a solution in which the object is dissolved, so that the object is deposited on the surface of the void-arranged structure. Then, after a solvent and an excess of the object are removed by washing and the void-arranged structure is dried, characteristics of the object are measured using the measuring apparatus described above.

In the present invention, various publicly known methods can be used to hold the object on the void-arranged structure. For example, the object may be deposited on the void-arranged structure either directly or through a supporting film. To realize high measurement sensitivity and carry out measurement with high reproducibility by reducing variation in measurement, it is preferable that the object be directly deposited on the surface of the void-arranged structure.

The cases of direct deposition of the object on the void-arranged structure include not only the case of forming a chemical bond directly between the surface of the void-arranged structure and the object, but also the case of bonding the object to a host molecule bonded in advance to the surface of the void-arranged structure. Examples of the chemical bond include a covalent bond (e.g., covalent bond between metal and thiol group), a Van der Waals bond, an ionic bond, a metallic bond, and a hydrogen bond. The chemical bond is preferably a covalent bond. A host molecule is a molecule or the like to which the object can be specifically bonded. Examples of a combination of the host molecule and the object include antigen and antibody, sugar chain and protein, lipid and protein, low molecular compound (ligand) and protein, protein and protein, and single-stranded DNA and single-stranded DNA.

For direct deposition of the object on the void-arranged structure, it is preferable to use a void-arranged structure in which at least part of its surface is formed of a conductor. For example, in the case of the void-arranged structure 1 illustrated in FIG. 2(*a*), at least one of the principal surface 10*a*, a side face 10*b*, and a void-portion side face 11*a* is formed of a conductor.

Here, the conductor is a substance (material) that conducts electricity. The conductor may be a metal or a semiconductor. Examples of the metal include a metal that can be bonded to a functional group (such as a hydroxy group, a thiol group, or a carboxyl group) of a compound, a metal that can be surface-coated with a functional group (such as a hydroxy group or an amino group), and an alloy of these metals. Specifically, the metal may be gold, silver, copper, iron, nickel, chromium, silicon, or germanium. The metal is preferably gold, silver, copper, nickel, or chromium, and more preferably gold. Using gold or nickel is advantageous in that particularly if the object contains a thiol group (—SH group), the thiol group can be bonded to the surface of the void-arranged structure. Using nickel is advantageous in that particularly if the object contains a hydroxy group (—OH) or a carboxyl group (—COOH), the functional group can be bonded to the surface of the void-arranged structure. Examples of the semiconductor include compound semiconductors, such as IV-group semiconductors (Si, Ge, etc.), II-VI-group semiconductors (ZnSe, CdS, ZnO, etc.), III-V-group semiconductors (GaAs, InP, GaN, etc.), IV-group compound semiconductors (SiC, SiGe, etc.), and I-III-VI-group semiconductors (CuInSe$_2$ etc.), and organic semiconductors.

Examples of the method for depositing the object on the void-arranged structure through a supporting film or the like include a method in which the object is deposited on a supporting film, such as a polyamide resin film, attached to the surface of the void-arranged structure. Instead of using a supporting film, an air-tight or fluid-tight container may be used to measure a fluid or a material dispersed in a fluid.

Embodiment 1

Figure 3:
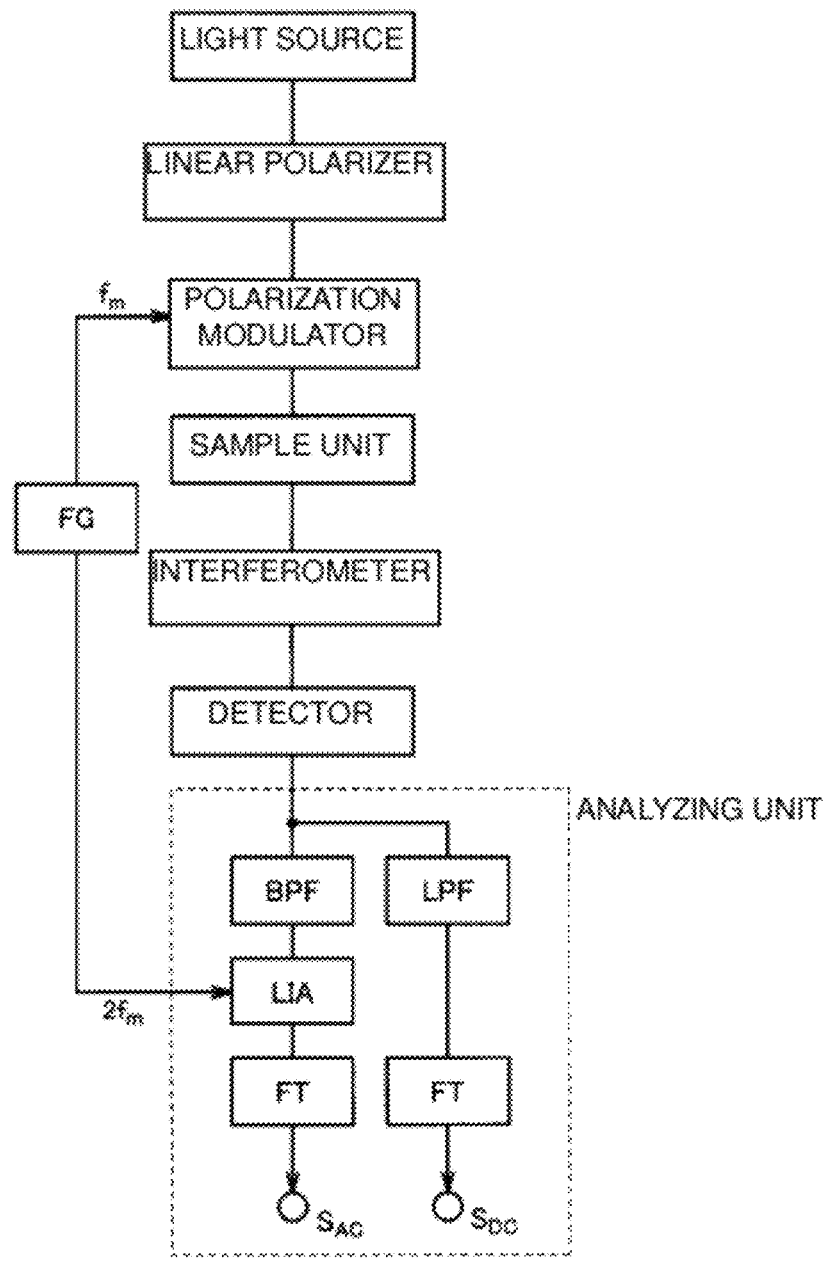
FIG. 3 is a schematic diagram illustrating a measuring method and apparatus according to Embodiment 1.

FIG. 3 is a schematic diagram for explaining a measuring method and apparatus according to the present embodiment. In the measuring method and apparatus illustrated in FIG. 3, the polarization state of linearly polarized electromagnetic waves is modulated by a polarization modulator into two different polarization states, and the resulting electromagnetic waves are swept by an interferometer (described below) with a frequency smaller than the modulation frequency, so that the first frequency characteristic and the second frequency characteristic are detected. For example, a Fourier transform infrared spectrophotometer (FT-IR) can be used which includes all components of the measuring apparatus of FIG. 3, except the polarization modulator and a function generator (FG). The measuring method and apparatus illustrated in FIG. 3 will now be described in detail.

First, electromagnetic waves emitted from a light source (which may either be a white light source or a tunable laser) are introduced into a linear polarizer (which may be removed if the light source provides a high degree of linear polarization). The electromagnetic waves emitted from the linear polarizer are linearly polarized electromagnetic waves having an intensity $P_0(v)$, where $v$ represents a wave number, which is the reciprocal of a wavelength.

Next, the electromagnetic waves are introduced into the polarization modulator typified by a photo-elastic modulator (PEM). An external signal (e.g., voltage generated by the functional generator) is applied to the polarization modulator at a frequency fm. The electromagnetic waves emitted from the polarization modulator are modulated in two different polarization directions at a frequency 2fm. Here, the two polarization directions are referred to as the X-axis direction and the Y-axis direction.

As a value representing a characteristic of the polarization modulator, a phase difference between two polarization directions to be generated is designated as $\Delta_0(v)$. An ideal polarization modulator generates polarizations 90° apart for every wave number, and its characteristic is represented by $\Delta_0(v)=0.5$. When the electromagnetic waves emitted from the polarization modulator are introduced into a sample, the resulting intensity $P_{OUT}(v,t)$ contains information about a transmittance Ty (transmittance of an electromagnetic wave polarized in the Y-axis direction) and a transmittance Tx (transmittance of an electromagnetic wave polarized in the X-axis direction) for the respective two polarization directions. $P_{OUT}(v,t)$ can be expressed by the following equation (2) using a Bessel function:

[Numerical Expression 2]

$$P_{OUT}(v, t) = \frac{1}{2}P_0(v)[T_X(v) + T_Y(v) + J_0(2\pi\Delta_0(v))\{T_X(v) - T_Y(v)\}] + \frac{1}{2}P_0(v)\left[2\sum_{k=0}^{\infty} J_{2k}(2\pi\Delta_0(v))\{T_X(v) - T_Y(v)\}\cos(4\pi f_m t)\right]$$ (2)

where t is the length of time required for scanning of the interferometer, $J_0$ is a zero-order Bessel function, and $J_{2k}$ is an even-order Bessel function.

When scanning of the interferometer is performed at a frequency sufficiently slower than the frequency fm (at a scanning speed of "u"), an interferogram F(x,t) which contains information about Ty and Tx is detected by a detector. The equation x=2ut holds true here. The interferogram F(x,t) can be expressed by the following equation (3):
[Numerical Expression 3]

$$F(x,t) = \int P_{OUT}(v,t)\cos(2\pi\mu x)dv$$ (3)

An output signal from the detector is divided into two output signals, one of which is lock-in-detected (LIA) through a band-pass filter (BPF) having a frequency range centered on the frequency 2fm. A reference signal in the lock-in detection has the frequency 2fm. With the band-pass filter and the lock-in detection, the fourth- and higher-order Bessel functions can be ignored. The lock-in-detected signal is Fourier-transformed (FT) into a signal, which is referred to as a signal $S_{AC}(v)$. The other of the output signals is Fourier-transformed (FT) through a low-pass filter (LPF) into a signal, which is referred to as a signal $S_{DC}(v)$. Ideally, the two paths in an analyzing unit are equal in gain and there is no phase difference therebetween. $S_{AC}(v)$ and $S_{DC}(v)$ can be expressed by the following equations (4):
[Numerical Expression 4]

$$S_{AC}(v) = 2J_2(2\pi\Delta_0(v))\{T_X(v) - T_Y(v)\}$$

$$S_{DC}(v) = T_X(v) + T_Y(v) + J_0(2\pi\Delta_0(v))\{T_X(v) - T_Y(v)\}$$ (4)

The ratio S(v) between the two signals $S_{AC}(v)$ and $S_{DC}(v)$ can be expressed by the following equation (5):

$$S(v) = S_{AC}(v)/S_{DC}(v)$$ (5)

An approximate equation which assumes an ideal polarization modulator ($\Delta_0(v)=0.5$) in equation (5) is as follows:

$$S = \{0.97Tx - 0.97Ty\}/\{0.696Tx + 1.304Ty\}$$ (6)

This equation is obtained by substituting a=0.97, b=−0.97, c=0.696, and d=1.304 into equation (1).

After an interferogram is measured while the polarization directions of electromagnetic waves are being switched by the polarization modulator, the measured interferogram is analyzed by the analyzing unit. Thus, a difference spectrum S(v) can be obtained from one interferogram. Then, for example, after S(v) is measured for various quantities of an object in advance, peak values of S(v) are determined to obtain a calibration curve, and then a value obtained as a result of actual measurement is compared with the calibration curve. It is thus possible to calculate, for example, the quantity of the object.

In the measuring apparatus illustrated in FIG. 3, for example, a Michelson interferometer or a Fabry-Perot interferometer can be used as the interferometer. When the measuring apparatus includes the interferometer, a high-pressure mercury lamp or high-temperature ceramic can be used as the light source. A wire grid can be used as the linear polarizer. A photo-elastic modulator (PEM) can be used as the polarization modulator. Examples of the detector include bolometers, such as a silicon bolometer and a germanium bolometer, and a pyroelectric sensor.

Although the linear polarizer is disposed between the light source and the sample unit in the measuring apparatus illustrated in FIG. 3, the linear polarizer may be disposed between the sample unit and the detector. For example, in this case, a non-polarized or circularly polarized electromagnetic wave emitted from the light source is divided into two after passing through the void-arranged structure in the sample unit. Then, the two waves are converted, for example, to two linearly polarized electromagnetic waves of different polarization directions as they pass through the linear polarizer. Thus, the frequency characteristics (first frequency characteristic and second frequency characteristic) of the respective electromagnetic waves can be detected.

Although FIG. 3 illustrates an apparatus configuration in which the interferometer is disposed between the sample unit and the detector, the interferometer may be disposed between the light source and the sample unit.

If the light source or the detector has a frequency sweep function, the measuring apparatus does not have to have the interferometer. For example, a measuring apparatus without an interferometer can be used which includes, as a source of electromagnetic waves, a laser source capable of emitting laser light produced by difference-frequency mixing of two laser beams of different wavelengths, a quantum cascade laser capable of adjusting the emission wavelength by controlling the operating temperature or applied current, or a plurality of lasers with slightly different wavelengths (e.g., quantum cascade lasers with fixed emission wavelengths).

In the measuring apparatus illustrates FIG. 3, polarization is typically controlled by the polarization modulator and frequency-related information can be obtained by interferometer sweep or frequency sweep. With the polarization modulator, information on both Ty and Tx can be obtained by one sweep. In other words, a difference spectrum can be obtained from one interferogram.

A measuring apparatus of Embodiment 2 (described below) does not have a polarization-related modulation function, such as a polarization modulator. In this case, unlike Embodiment 1, each of Ty and Tx requires one sweep. However, Embodiment 2 requires fewer sweeps than the related art.

Embodiment 2

Figure 4A:
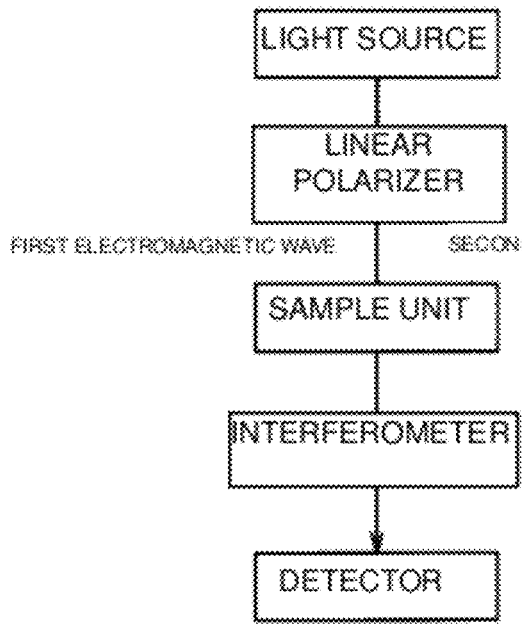
FIGS. 4(a) and 4(b) are schematic diagrams illustrating a measuring method and apparatus according to Embodiment 2.
Figure 4B:
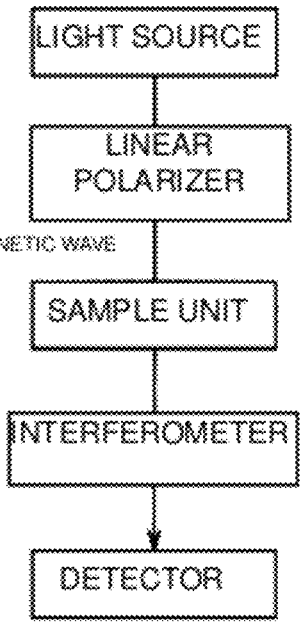

FIGS. 4(a) and 4(b) are schematic diagrams for explaining another measuring method and apparatus according to the present invention. Embodiment 2 is different from Embodiment 1 in that it does not have a high-speed polarization control function, typified by a polarization modulator. Embodiment 2 is the same as Embodiment 1 in that, for detecting frequency characteristics of electromagnetic waves transmitted through the void-arranged structure, a first frequency characteristic and a second frequency characteristic are measured to obtain a difference spectrum S(v) using equation (1).

In the measuring method and apparatus illustrated in FIGS. 4(a) and 4(b), a frequency characteristic of a first electromagnetic wave is measured in a first measurement state (FIG. 4(a)). Then, the light source or the linear polarizer is adjusted to set a second measurement state (FIG. 4(b)), in which a frequency characteristic of a second electromagnetic wave is measured. The measuring method and apparatus illustrated in FIGS. 4(a) and 4(b) will now be described in detail.

An electromagnetic wave emitted from the light source (which may either be a white light source or a tunable laser) is introduced into the linear polarizer (which may be removed if the light source provides a high degree of linear polarization). The electromagnetic wave emitted from the linear polarizer is a linearly polarized electromagnetic wave, which is applied to the void-arranged structure on which a sample is held. Then, the electromagnetic wave transmitted through the void-arranged structure is detected to measure the frequency characteristic of the first electromagnetic wave. Here, the polarization direction of the first electromagnetic wave is referred to as the Y-axis direction, and the measured frequency characteristic is represented by Ty. Next, either the polarization direction of an electromagnetic wave emitted from the light source or the linear polarizer is adjusted, and the polarization direction preferably orthogonal to that in the first measurement state is selected. Then similarly, the frequency characteristic of the second electromagnetic wave is measured. Here, the polarization direction of the second electromagnetic wave is referred to as the X-axis direction, and the measured frequency characteristic is represented by Tx. For the resulting Ty and Tx, a difference spectrum $S(v)$ can be obtained from equation (1) (or equation (6)). Then, for example, after $S(v)$ is measured for various quantities of an object in advance, peak values of $S(v)$ are determined to obtain a calibration curve, and then a value obtained as a result of actual measurement is compared with the calibration curve. It is thus possible to calculate the quantity of the object.

In the measuring apparatus illustrated in FIGS. 4(a) and 4(b), for example, a Michelson interferometer or a Fabry-Perot interferometer can be used as the interferometer. Examples of the light source include a high-pressure mercury lamp, a high-temperature ceramic, a laser source capable of emitting laser light produced by difference-frequency mixing of two laser beams of different wavelengths, a quantum cascade laser capable of varying the emission wavelength by controlling the operating temperature or applied current, and a plurality of lasers with slightly different wavelengths (e.g., quantum cascade lasers with fixed emission wavelengths). Examples of the detector include bolometers, such as a silicon bolometer and a germanium bolometer, and a pyroelectric sensor.

Figure 5A:
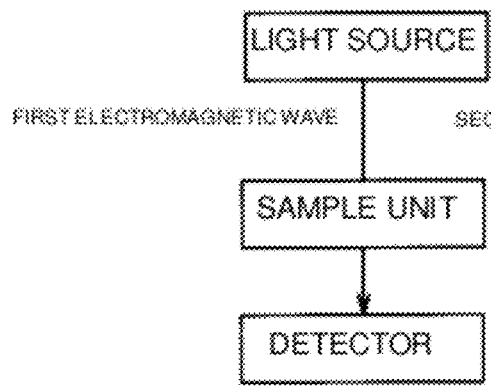
FIGS. 5(a) and 5(b) are schematic diagrams illustrating another measuring method and apparatus according to Embodiment 2.
Figure 5B:
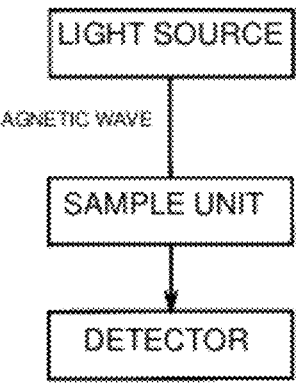

Although FIGS. 4(a) and 4(b) illustrate an apparatus configuration in which the interferometer is disposed between the sample unit and the detector, the interferometer may be disposed between the light source and the sample unit. As illustrated in FIGS. 5(a) and 5(b), if the light source or the detector has a frequency sweep function, the measuring apparatus does not have to have the interferometer. In the case of having no interferometer, the measuring apparatus can use, as a light source that emits electromagnetic waves, a laser source capable of emitting laser light produced by difference-frequency mixing of two laser beams of different wavelengths, a quantum cascade laser capable of adjusting the emission wavelength by controlling the operating temperature or applied current, or a plurality of lasers with slightly different wavelengths (e.g., quantum cascade lasers with fixed emission wavelengths). In the measuring apparatus illustrated in FIGS. 5(a) and 5(b), it is preferable that a linear polarizer, such as a wire grid exhibiting a high extinction ratio, be disposed between the light source and the sample unit to increase the extinction ratio of linear polarization of an electromagnetic wave incident on the sample.

In the measuring apparatus illustrated in FIGS. 4(a) and 4(b), the light source is not limited to a specific one. The first electromagnetic wave and the second electromagnetic wave are generated by controlling the light source or the linear polarizer, so that Ty and Tx are measured separately. The difference spectrum is determined by computer-processing the measured Ty and Tx.

The apparatuses illustrated in both FIG. 3 and FIGS. 4(a) and 4(b) are capable of detecting frequency characteristics of electromagnetic waves transmitted through the void-arranged structure.

The measuring methods of Embodiments 1 and 2 use measuring apparatuses of frequency sweep type. However, the measuring method of the present invention may use a measuring apparatus of time sweep type, such as a time-domain terahertz spectrometer (THz-TDS) or an oscilloscope. In this case, responses of electromagnetic waves transmitted through the void-arranged structure are measured in a time domain to determine impulse responses, which are Fourier-transformed into frequency characteristics by a computer. Thus, a measurement similar to that in the measuring methods of Embodiments 1 and 2 can be performed.

Embodiment 3

The present embodiment is an example in which, in the measuring method of the present invention, a frequency characteristic of the void-arranged structure obtained by applying an electromagnetic wave to the void-arranged structure in a predetermined first direction with respect to the principal surface of the void-arranged structure is detected as the first frequency characteristic, and a frequency characteristic of the void-arranged structure obtained by applying an electromagnetic wave to the void-arranged structure in a second direction different from the first direction with respect to the principal surface of the void-arranged structure is detected as the second frequency characteristic.

Figure 6:
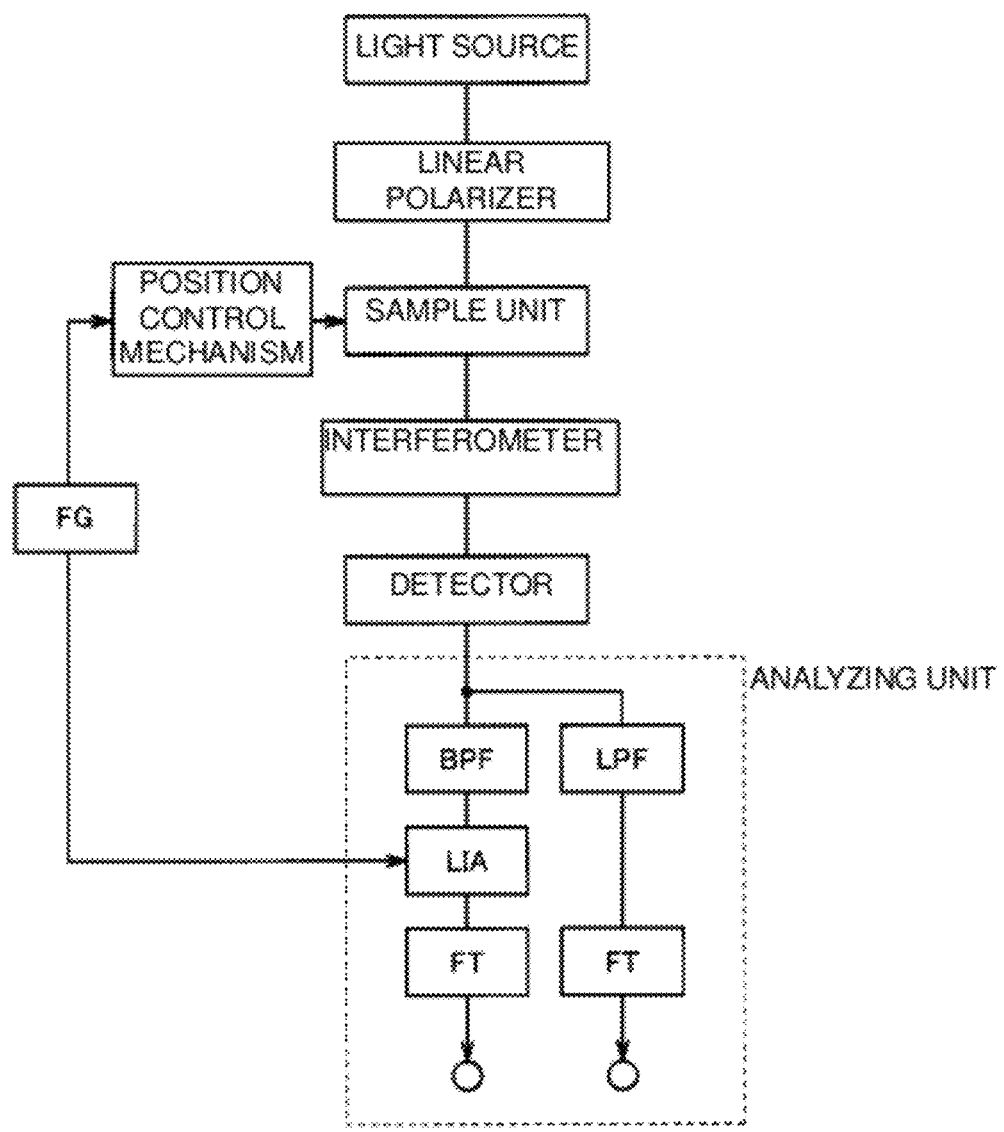
FIG. 6 is a schematic diagram illustrating a measuring method and apparatus according to Embodiment 3.

FIG. 6 illustrates a measuring apparatus of the present embodiment. The measuring apparatus used in the present embodiment includes a position control mechanism capable of controlling the position of the void-arranged structure. The position control mechanism preferably has a rotating function that can rotate the void-arranged structure about the rotation axis. For example, the rotating function is a function that can rotate the void-arranged structure at a constant speed or periodically in a reciprocating manner.

Although the measuring apparatus illustrated in FIG. 6 is an apparatus in which the interferometer is disposed between the sample unit and the detector, the interferometer may be disposed, for example, between the light source and the sample unit. If the light source or the detector has a frequency sweep function, the measuring apparatus does not have to have the interferometer (the same applies to Embodiments 4 and 5 described below).

As illustrated in FIG. 6, electromagnetic waves emitted from the light source (e.g., white light source or tunable laser) are introduced into the linear polarizer (which may be removed if the light source provides a high degree of linear polarization). The electromagnetic waves emitted from the linear polarizer are linearly polarized electromagnetic waves having an intensity $P_0(v)$ and are applied to the sample unit. The sample unit includes the void-arranged structure alone or the void-arranged structure on which an object is deposited. Note that v represents a wave number, which is the reciprocal of a wavelength.

The void-arranged structure in the sample unit is connected to a rotating stage. The position control mechanism controls the position of the void-arranged structure with respect to the propagation direction and the polarization direction of electromagnetic waves. By the position control mechanism, the void-arranged structure is placed at a (1) position where the principal surface of the void-arranged structure is parallel to the polarization direction of the electromagnetic wave (including a position where the principal surface of the void-arranged structure is perpendicular to the propagation direction of the electromagnetic wave) or a (2) position where the principal surface of the void-arranged structure is not parallel to the polarization direction of the electromagnetic wave.

For the positions (1) and (2) described above, a positional relationship between an electromagnetic wave and the void-arranged structure will be explained with reference to FIGS. 7(a), 7(b), 8(a) and 8(b). In FIGS. 7(a), 7(b), 8(a) and 8(b), a polarization direction E of a linearly polarized electromagnetic wave emitted from the light source is the Y-axis direction, and the propagation direction of the linearly polarized electromagnetic wave is the Z-axis direction.

Figure 7A:
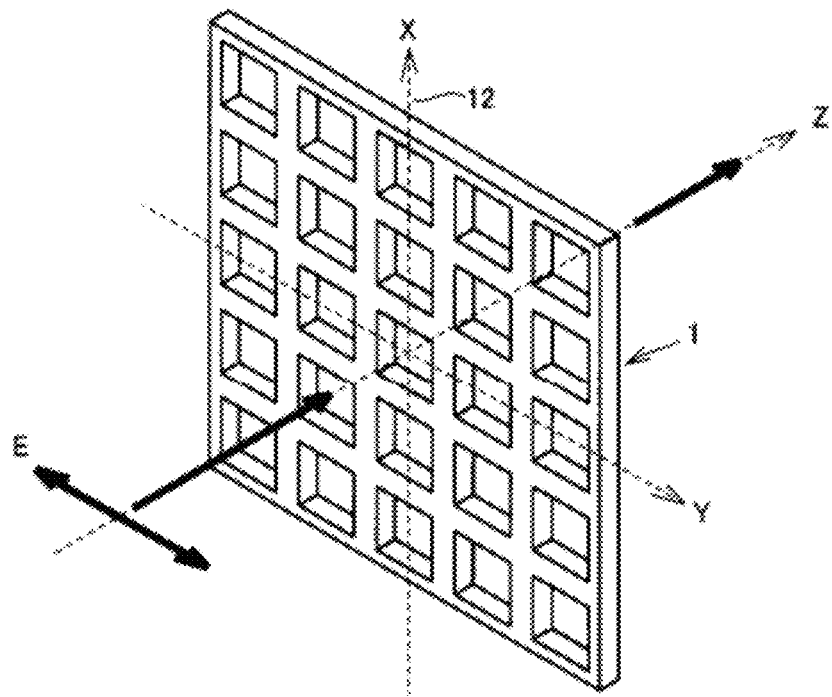
FIGS. 7(a) and 7(b) are schematic diagrams illustrating a positional relationship between the void-arranged structure and a direction of an electromagnetic wave in Embodiment 3.

Position where Principal Surface of Void-Arranged Structure is Parallel to Polarization Direction of Electromagnetic Wave A position where the principal surface of the void-arranged structure is parallel to the polarization direction of the electromagnetic wave is a position where the principal surface of the void-arranged structure 1 is perpendicular to the propagation direction of the electromagnetic wave (Z-axis direction) (i.e., perpendicular to a plane parallel to the XY plane) (FIGS. 7(a) and (b)) or a position (not shown) reached by rotating the void-arranged structure 1 from this position by a predetermined angle about a rotation axis (e.g., Y-axis) parallel to the polarization direction E of the electromagnetic wave. Normally, no dip waveform appears in a frequency characteristic (second frequency characteristic) obtained in this case. Even in the cases where the applied electromagnetic wave is not a linearly polarized electromagnetic wave, normally, no dip waveform or only a small dip waveform appears in the second frequency characteristic.

(2) Position where Principal Surface of Void-Arranged Structure is not Parallel to Polarization Direction of Electromagnetic Wave A position where the principal surface of the void-arranged structure is not parallel to the polarization direction of the electromagnetic wave is any position except the position (1) described above. That is, the position (2) is a position reached by rotating the void-arranged structure 1 from the position where the principal surface of the void-arranged structure 1 is perpendicular to the propagation direction of the electromagnetic wave (Z-axis direction) (FIGS. 7(a) and (b)) by a predetermined angle (except 0°) about a rotation axis not parallel to the polarization direction of the electromagnetic wave. For example, this position is a position (FIGS. 8(a) and (b)) reached by rotating the void-arranged structure 1 from the position in FIGS. 7(a) and 7(b) by an angle θ about a rotation axis 12 (X-axis) perpendicular to the polarization direction E (Y-axis direction) and the propagation direction (Z-axis direction) of the electromagnetic wave. Normally, a dip waveform appears in a frequency characteristic (first frequency characteristic) obtained in this case.

In the present embodiment, the position control mechanism causes the void-arranged structure to periodically reciprocate between the (1) position where the principal surface of the void-arranged structure is parallel to the polarization direction of the electromagnetic wave (including a position where the principal surface of the void-arranged structure is perpendicular to the propagation direction of the electromagnetic wave) and the (2) position where the principal surface of the void-arranged structure is not parallel to the polarization direction of the electromagnetic wave.

A more specific example will be described in which the position control mechanism has a function (rotating function) of rotating the rotating stage on which the void-arranged structure is mounted. The void-arranged structure mounted on the rotating stage is rotated by the position control mechanism having the rotating function from the (1) position (illustrated in FIGS. 7(a) and 7(b)) where the principal surface of the void-arranged structure is perpendicular to the propagation direction of the electromagnetic wave to the (2) position (illustrated in FIGS. 8(a) and 8(b)) where the principal surface of the void-arranged structure forms the angle θ with the polarization direction of the electromagnetic wave. Then, by reverse rotation, the void-arranged structure is returned from the position illustrated in FIGS. 8(a) and 8(b) to the position illustrated in FIGS. 7(a) and 7(b). For example, an external signal (e.g., voltage generated by a signal generator FG) is applied to the position control mechanism at the frequency fm. One cycle of the reciprocating rotation takes place during one period (which is the reciprocal of fm in the length in time) of the external signal.

Figure 7B:
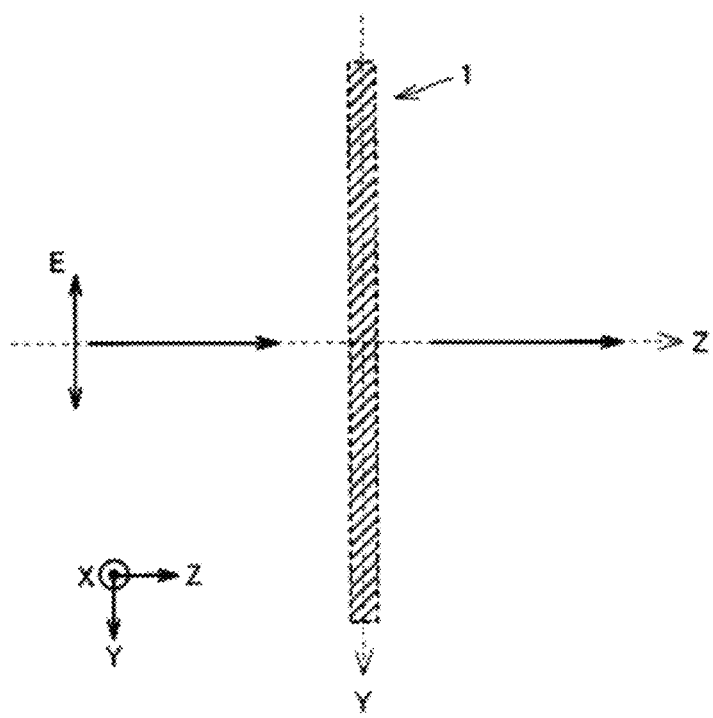
Figure 8A:
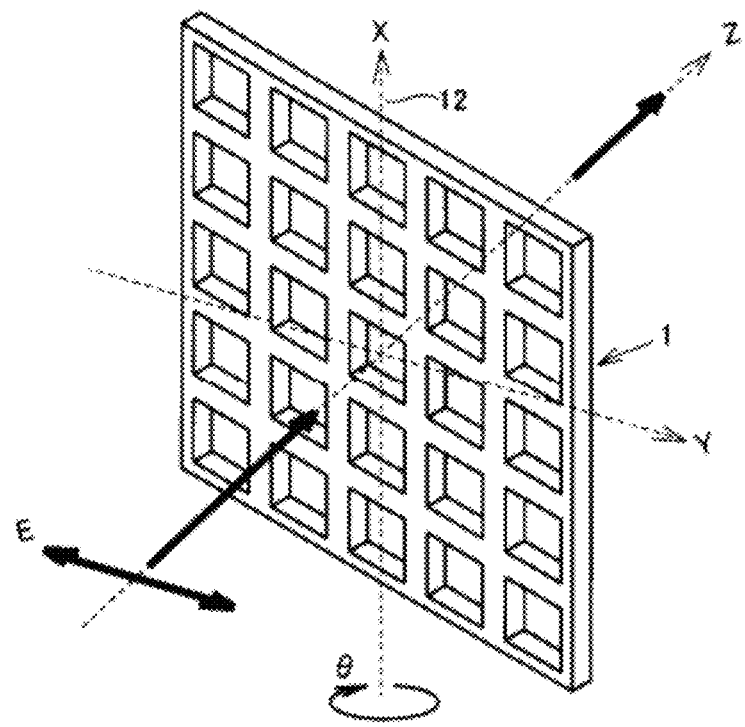
FIGS. 8(a) and 8(b) are schematic diagrams illustrating a positional relationship between the void-arranged structure and a direction of an electromagnetic wave in Embodiment 3.
Figure 8B:
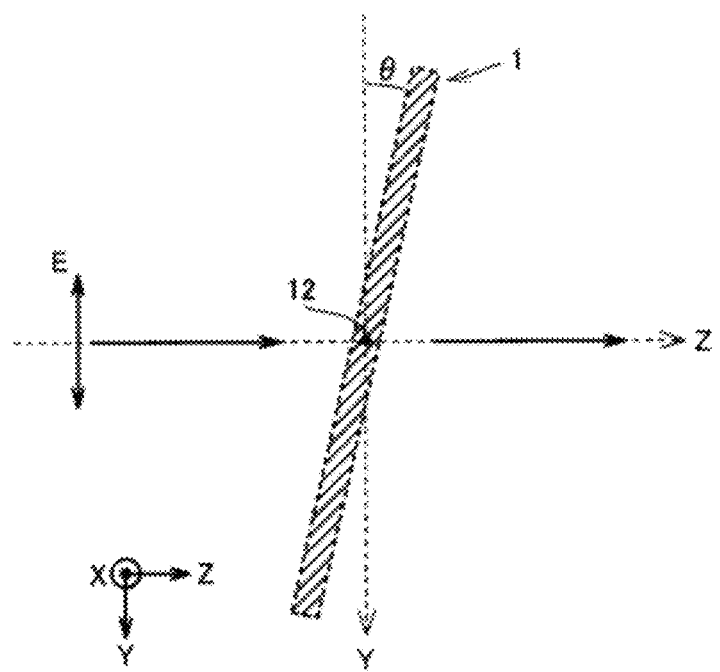

When the electromagnetic wave emitted from the linear polarizer is introduced into the sample, the resulting intensity $P_{OUT}(v,t)$ contains information about transmittances (Tv and Tt) at the (1) position (illustrated in FIGS. 7(a) and 7(b)) where the principal surface of the void-arranged structure is perpendicular to the propagation direction of the electromagnetic wave and the (2) position (illustrated in FIGS. 8(a) and 8(b)) where the principal surface of the void-arranged structure forms the angle θ with the polarization direction of the electromagnetic wave. $P_{OUT}(v,t)$ can be expressed by the following equation (2') obtained by substituting Tv for Tx in equation (2) and Tt for Ty in equation (2) using a Bessel function:

[Numerical Expression 5]

$$P_{OUT}(v, t) = \frac{1}{2}P_0(v)[T_V(v) + T_T(v) + J_0(2\pi\Delta)\{T_V(v) - T_T(v)\}] + \frac{1}{2}P_0(v)\left[2\sum_{k=0}^{\infty} J_{2k}(2\pi\Delta)\{T_V(v) - T_T(v)\}\cos(2\pi f_m t)\right] \quad (2')$$

where t is the length of time required for scanning of the interferometer, $J_0$ is a zero-order Bessel function, $J_{2k}$ is an even-order Bessel function, and Δ is a variable representing the degree of modulation of an incidence angle.

When scanning of the interferometer is performed at a frequency sufficiently slower than the frequency fm (at a scanning speed of "u"), an interferogram F(x,t) which contains information about Tv and Tt is detected by the detector. The equation x=2ut holds true here. The interferogram F(x,t) can be expressed by the following equation (3):

[Numerical Expression 6]

$$F(x,t) = \int P_{OUT}(v,t)\cos(2\pi vx)dv \quad (3)$$

An output signal from the detector is divided into two output signals, one of which is lock-in-detected (LIA) through the band-pass filter (BPF) having a frequency range centered on the frequency fm. A reference signal in the lock-in detection has the frequency fm. With the band-pass filter and the lock-in detection, the fourth- and higher-order Bessel functions can be ignored. The lock-in-detected signal is Fourier-transformed (FT) into a signal, which is referred to as a signal $S_{AC}(v)$. The other of the output signals is Fourier-transformed (FT) through the low-pass filter LPF into a signal, which is referred to as a signal $S_{DC}(v)$. Ideally, the two paths in the analyzing unit are equal in gain and there is no phase difference therebetween. $S_{AC}(v)$ and $S_{DC}(v)$ can be expressed by the following equations (4'):
[Numerical Expression 7]

$$S_{AC}(v)=2J_2(2\pi\Delta)\{T_V(v)-T_T(v)\}$$

$$S_{DC}(v)=T_V(v)+T_T(v)+J_0(2\pi\Delta)\{T_V(v)-T_T(v)\} \quad (4')$$

The ratio $S(v)$ between the two signals $S_{AC}(v)$ and $S_{DC}(v)$ can be expressed by the following equation (5):

$$S(v)=S_{AC}(v)/S_{DC}(v) \quad (5)$$

After an interferogram is measured while the direction of the void-arranged structure with respect to the electromagnetic wave is being switched by the position control mechanism, the measured interferogram is analyzed by the analyzing unit. Thus, a difference spectrum $S(v)$ can be obtained from one interferogram. Then, for example, after $S(v)$ is measured for various quantities of an object in advance, peak values of $S(v)$ are determined to obtain a calibration curve, and then a value obtained as a result of actual measurement is compared with the calibration curve. It is thus possible to calculate, for example, the quantity of the object.

Embodiment 4

A measuring apparatus used in the present embodiment includes an electromagnetic-wave emitting unit for applying electromagnetic waves to the void-arranged structure on which an object is held, and a branching filter capable of separating the electromagnetic waves emitted from the electromagnetic-wave emitting unit into a first electromagnetic wave for obtaining a first frequency characteristic and a second frequency characteristic for obtaining a second frequency characteristic.

The present embodiment is the same as Embodiment 3 in that it provides a method which measures a frequency characteristic (second frequency characteristic) of the void-arranged structure obtained by applying a linearly polarized electromagnetic wave to the void-arranged structure in a direction perpendicular to the principal surface of the void-arranged structure and a frequency characteristic (first frequency characteristic) of the void-arranged structure obtained by applying a linearly polarized electromagnetic wave to the void-arranged structure in a direction not perpendicular to the principal surface of the void-arranged structure, so that characteristics of an object can be measured from a difference spectrum between the measured frequency characteristics.

Figure 9:
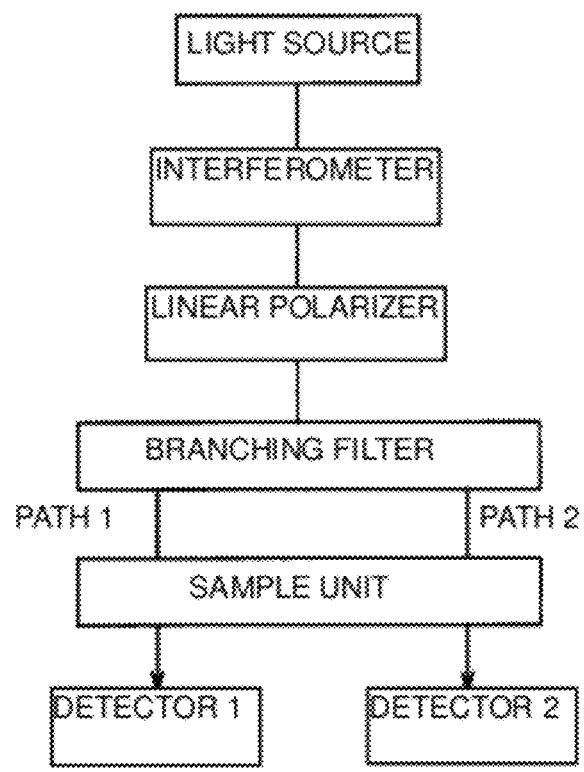
FIG. 9 is a schematic diagram illustrating a measuring method and apparatus according to Embodiment 4.

FIG. 9 illustrates an apparatus configuration of the present embodiment. As illustrated in FIG. 9, electromagnetic waves emitted from the light source pass through the interferometer and are introduced into the linear polarizer, which may be removed if the light source provides a high degree of linear polarization. The electromagnetic waves from the linear polarizer are linear polarizations (parallel to the Y-axis), which are separated into two paths by the branching filter. Note that equally separating the linear polarizations is advantageous in terms of ease of analysis.

Figure 10:
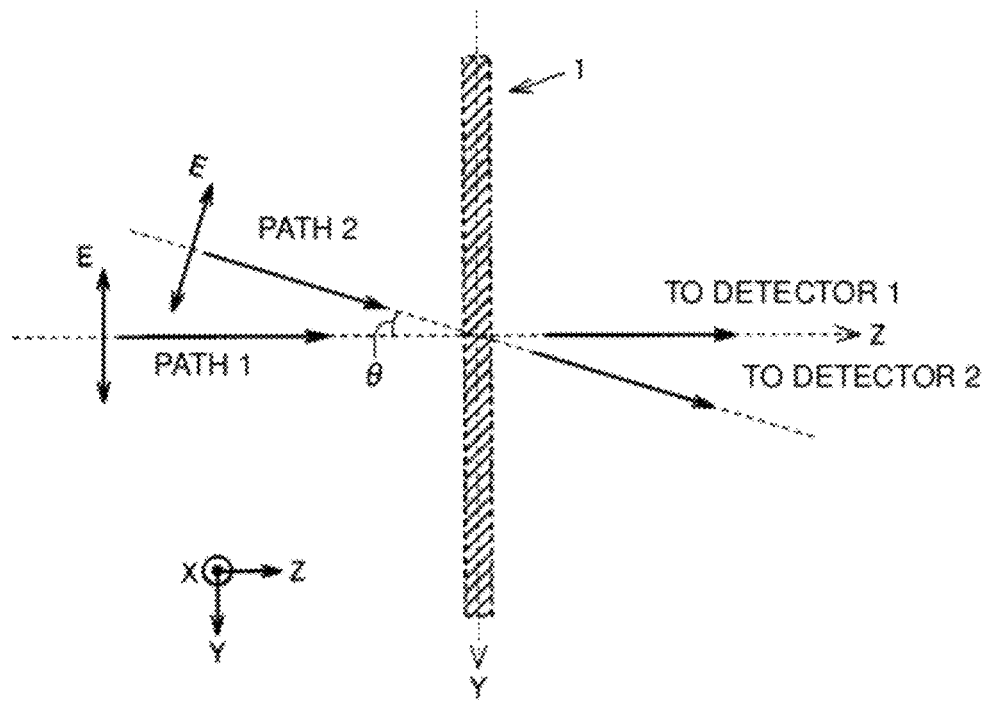
FIG. 10 is a schematic diagram illustrating a positional relationship between the void-arranged structure and directions of electromagnetic waves in Embodiment 4.

The two paths created by the branching filter are referred to as path 1 and path 2. As illustrated in FIG. 10, path 1 extends in a direction perpendicular to the principal surface of the void-arranged structure 1 (i.e., perpendicular to a plane parallel to the XY plane). An electromagnetic wave transmitted through the void-arranged structure 1 along path 1 is detected by detector 1. On the other hand, Path 2 extends in a direction not perpendicular to (i.e., in a slanting direction with respect to) the principal surface of the void-arranged structure 1. An electromagnetic wave transmitted through the void-arranged structure 1 along path 2 is detected by detector 2. It is important here that the polarization direction E of an incident electromagnetic wave does not coincide with the orientation of the rotation axis of the void-arranged structure.

A frequency characteristic detected by detector 1 in the present embodiment is equivalent to Tv in Embodiment 3, and a frequency characteristic detected by detector 2 in the present embodiment is equivalent to Tt in Embodiment 3. Therefore, it is possible to obtain a difference spectrum S and measure characteristics of an object in a manner similar to that of Embodiment 3. The present embodiment is advantageous in that the frequency characteristics Tv and Tt can be obtained by one frequency sweep or interferometer sweep.

Embodiment 5

A measuring apparatus used in the present embodiment includes a plurality of light sources and/or a plurality of detectors.

The present embodiment is the same as Embodiments 3 and 4 in that it provides a method which measures a frequency characteristic (second frequency characteristic) of the void-arranged structure obtained by applying a linearly polarized electromagnetic wave to the void-arranged structure in a direction perpendicular to the principal surface of the void-arranged structure and a frequency characteristic (first frequency characteristic) of the void-arranged structure obtained by applying a linearly polarized electromagnetic wave to the void-arranged structure in a direction not perpendicular to the principal surface of the void-arranged structure, so that characteristics of an object can be measured from a difference spectrum between the measured frequency characteristics.

Figure 11:
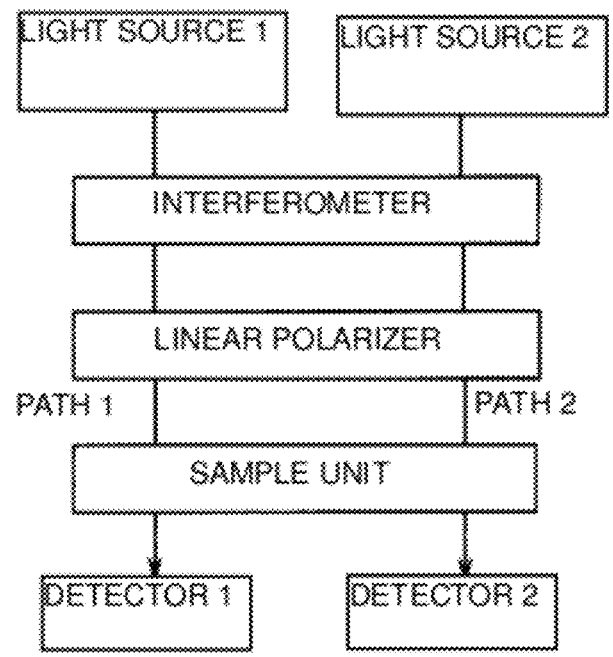
FIG. 11 is a schematic diagram illustrating a measuring method and apparatus according to Embodiment 5.

FIG. 11 illustrates an apparatus configuration of the present embodiment. Although FIG. 11 illustrates an example in which the interferometer and the linear polarizer are shared between the two paths, the interferometer and the linear polarizer may be provided for each light source. For higher accuracy of the measuring apparatus, it is preferable to synchronize the powers and frequencies of the light sources and the sensitivities of the detectors.

As illustrated in FIG. 11, electromagnetic waves emitted from light source 1 and light source 2 pass through the interferometer and are introduced into the linear polarizer, which may be removed if the light sources provide a high degree of linear polarization. Electromagnetic waves emitted from the linear polarizer are linear polarizations (parallel to the Y-axis).

As in Embodiment 4, path 1 extends in a direction perpendicular to the principal surface of the void-arranged structure 1 (i.e., perpendicular to a plane parallel to the XY plane). An electromagnetic wave transmitted through the void-arranged structure 1 along path 1 is detected by detector 1. On the other hand, Path 2 extends in a direction not perpendicular to (i.e., in a slanting direction with respect to) the principal surface of the void-arranged structure 1. An electromagnetic wave transmitted through the void-arranged structure 1 along path 2 is detected by detector 2 (see FIG. 10). It is important here that the polarization direction E of an incident electromagnetic wave does not coincide with the orientation of the rotation axis of the void-arranged structure.

A frequency characteristic detected by detector 1 in the present embodiment is equivalent to Tv in Embodiment 3, and a frequency characteristic detected by detector 2 in the present embodiment is equivalent to Tt in Embodiment 3.

Therefore, it is possible to obtain a difference spectrum S and measure characteristics of an object in a manner similar to that of Embodiment 3. That is, the difference spectrum S is defined by the following equation (1') obtained by substituting Tv for Tx in equation (1) and Tt for Ty in equation (1):

[Numerical Expression 8]

$$S(v) = \frac{aT_V(v) + bT_T(v)}{cT_V(v) + dT_T(v)} \quad (1')$$

where v is a wave number which is the reciprocal of a wavelength, and a, b, c, and d are any constants.

The present embodiment is advantageous in that the frequency characteristics Tv and Tt can be obtained by one frequency sweep or interferometer sweep.

Note: 1

The measuring method of the present invention is applicable not only to the case of detecting a frequency characteristic of an electromagnetic wave transmitted through (or forward-scattered by) the void-arranged structure, but also to the case of detecting a frequency characteristic of an electromagnetic wave reflected (or backward-scattered) by the void-arranged structure. Although a dip waveform appears in a frequency characteristic of a transmittance spectrum, a peak waveform appears in the case of a reflection spectrum. By selecting appropriate constants in equation (1) described above, a difference spectrum S between reflection spectra can be formed into a peak waveform having an upwardly protruding shape, as in the case of the difference spectrum S between transmittance spectra. By using this, computations for transmittance and reflection spectra may be made into a common one.

EXAMPLES

Although the present invention will be described in further detail with examples, the present invention is not limited to the examples.

Example 1

Figure 12:
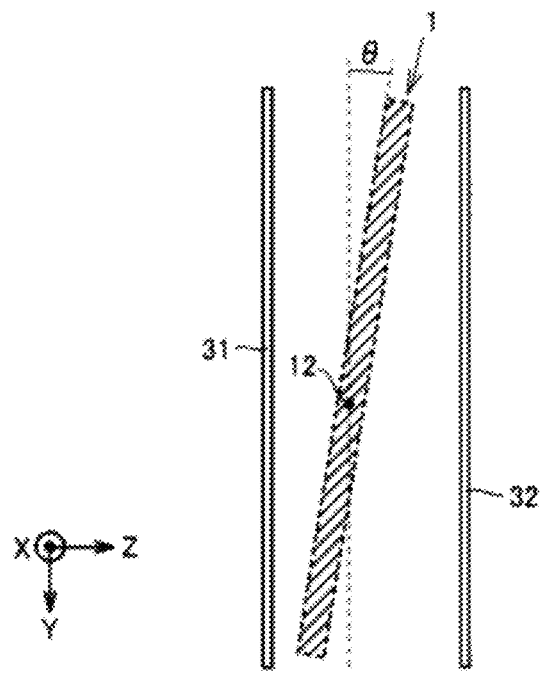
FIG. 12 is a schematic diagram for explaining models of simulation calculation in examples.

As illustrated in FIG. 12, for a model in which the void-arranged structure (metal mesh) 1 is placed between ports 31 and 32 spaced by a distance of 460 µm, periodic boundary conditions were applied in the X-axis direction (perpendicular to the plane of the drawing) and the Y-axis direction in FIG. 12, and a simulation calculation of frequency characteristics was performed using an electromagnetic field simulator, MicroStripes (made by CST AG).

The distance between the port 31 and the center of gravity of the metal mesh 1 was set to 230 µm, and the distance between the port 32 and the center of gravity of the metal mesh 1 was set to 230 µm. The ports 31 and 32 each are a 60-µm-thick plate having a 1.3-mm-square principal surface. The port 31 is an electromagnetic-wave emitting member which also serves to measure the intensity of an electromagnetic wave applied to the metal mesh 1. The port 32 is a measuring member that measures the intensity of an electromagnetic wave transmitted through the metal mesh. The metal mesh 1 was placed by being rotated from a state (θ=0°) where its principal surface is perpendicular to the propagation direction of the electromagnetic wave (Z-axis direction) about the rotation axis 12, which is a straight line that passes through the center of gravity of the metal mesh 1 and is parallel to the X-axis. An angle (θ in FIG. 12) by which the metal mesh was rotated was set to 9°.

In the present example, a model for the void-arranged structure was a metal mesh made entirely of copper and having square openings arranged in a square grid pattern, such as that illustrated in the schematic diagram of FIGS. 2(a) and 2(b). The metal mesh is 260 µm in grid spacing ("s" in FIG. 2(b)), 180 µm in opening size ("d" in FIG. 2(b)), 60 µm in thickness, and 1.3-mm-square plate-like in overall shape. A model for an object was a 1.3-mm-square plate-like dielectric film having a relative dielectric constant of 2.4, a dielectric loss tangent of 0, and a thickness of 5 µm.

In the present example, a simulation calculation was performed on the assumption of the apparatus configuration described with reference to FIG. 3. Specifically, in the sample unit illustrated in FIG. 3, the dielectric film was firmly attached to a side of the void-arranged structure close to the light source (i.e., a side close to the port 31 in FIG. 12). When an electromagnetic wave (first electromagnetic wave) propagating in the Z-axis direction in FIG. 12 and polarized in the Y-axis direction in FIG. 12 was applied, a frequency characteristic (Ty) of the electromagnetic wave transmitted through the metal mesh was calculated as a first frequency characteristic. Also, when an electromagnetic wave (second electromagnetic wave) propagating in the Z-axis direction in FIG. 12 and polarized in the X-axis direction in FIG. 12 was applied, a frequency characteristic (Tx) of the electromagnetic wave transmitted through the metal mesh was calculated as a second frequency characteristic. The calculated Ty and Tx are shown in FIG. 14.

Figure 14:
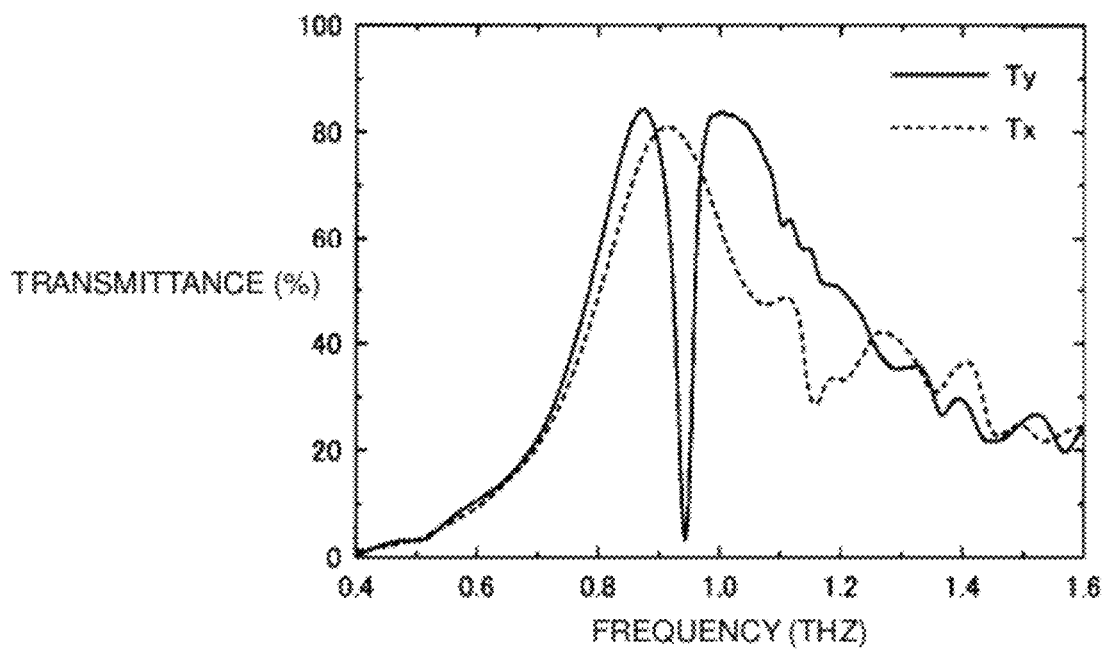
FIG. 14 is a graph showing a transmittance spectrum Ty and a transmittance spectrum Tx in Example 1.
Figure 15:
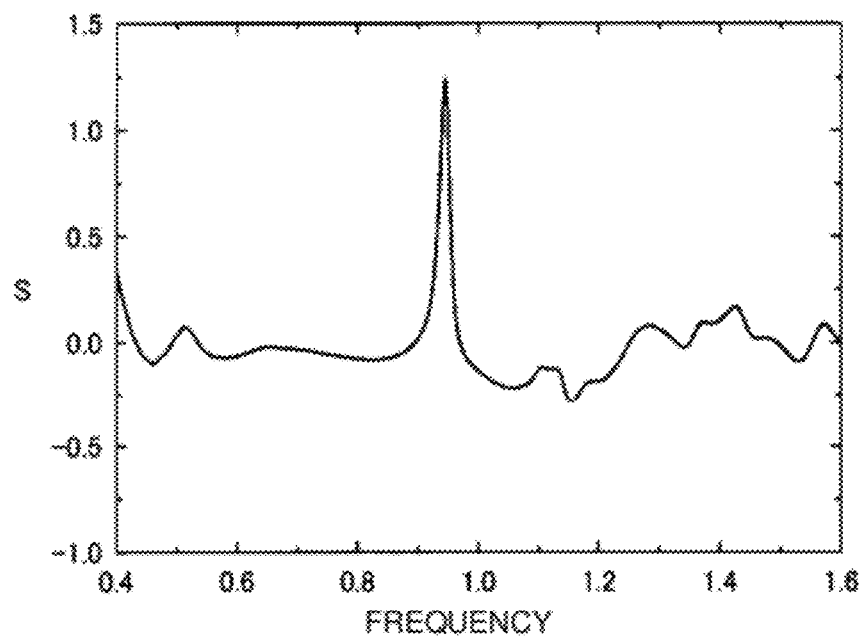
FIG. 15 is a graph showing a difference spectrum S in Example 1.

A difference spectrum S between Ty (first frequency characteristic) and Tx (second frequency characteristic) of FIG. 14 is shown in FIG. 15. The difference spectrum S was determined by equation (6) described above.

A positive peak appearing at around 0.93 THz in FIG. 15 represents characteristics of the object. For example, after S(v) is measured for various quantities of the object in advance, peak values of S(v) are determined to obtain a calibration curve, and then a value obtained as a result of actual measurement is compared with the calibration curve. It is thus possible to calculate, for example, the quantity of the object.

Comparative Example 1

Figure 13:
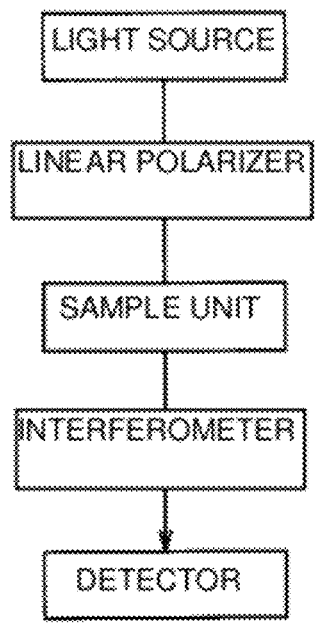
FIG. 13 is a schematic diagram for explaining a conventional measuring method and apparatus used as a model in Comparative Example 1.

FIG. 13 is a schematic diagram for explaining a conventional measuring method and apparatus used as a model in Comparative Example 1. The configuration of this measuring apparatus is a configuration of a conventional spectroscopic measuring apparatus, typified by a Fourier transform infrared spectrophotometer (FT-IR). The measuring apparatus illustrated in FIG. 13 includes an interferometer, which is disposed between a sample unit and a detector.

In Comparative Example 1, the polarization direction of an electromagnetic wave applied to a metal mesh was set only to the Y-axis direction in FIG. 12, and the polarization direction of an electromagnetic wave detected at the ports 31 and 32 was also set to the Y-axis direction. Then, a simulation calculation of frequency characteristics was performed using an electromagnetic field simulator, MicroStripes (made by CST AG).

First, a calculation was made to determine a frequency characteristic ($Back_R$) obtained when nothing was placed in the sample unit in FIG. 13, and a frequency characteristic (Ref) obtained when only the metal mesh was placed in the sample unit in FIG. 13. Then, Ref was divided by $Back_R$ to determine a transmittance spectrum ($T_{Ref}$) in the case where only the metal mesh was placed. The calculation result is shown in FIG. 16.

Similarly, a calculation was made to determine a frequency characteristic ($Back_S$) obtained when nothing was placed in the sample unit in FIG. 13, and a frequency characteristic (Sam) obtained when the metal mesh with a dielectric film firmly attached thereto was placed in the sample unit in FIG. 13. Then, Sam was divided by $Back_S$ to determine a transmittance spectrum ($T_{Sam}$) in the case where the metal mesh with the dielectric film firmly attached thereto was placed. The calculation result is shown in FIG. 16.

Figure 16:
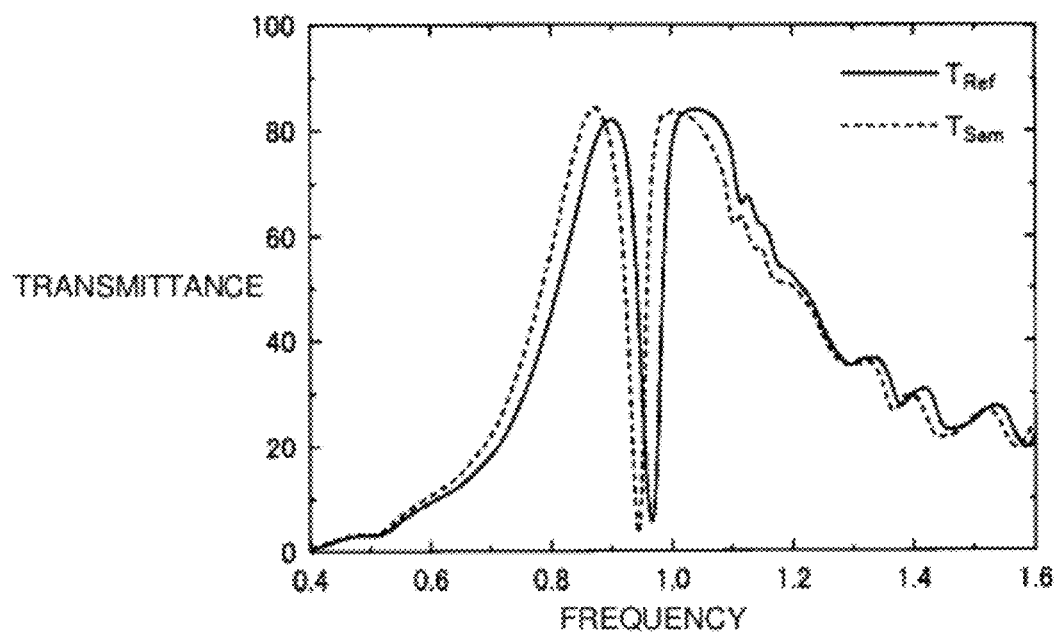
FIG. 16 is a graph showing a transmittance spectrum $T_{Ref}$ and a transmittance spectrum $T_{Sam}$ in Comparative Example 1.
Figure 17:
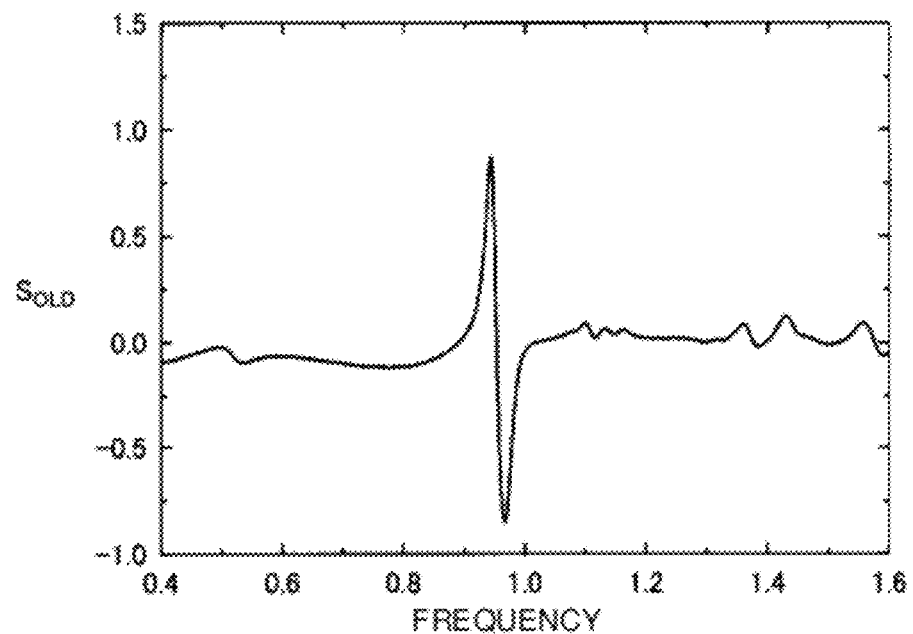
FIG. 17 is a graph showing a difference spectrum $S_{OLD}$ in Comparative Example 1.

A comparison between $T_{Ref}$ and $T_{Sam}$ in FIG. 16 reveals that the frequency characteristic varies depending on the presence of the object (dielectric film). A difference spectrum $S_{OLD}$ between $T_{Ref}$ and $T_{Sam}$ in the conventional method in FIG. 16 is shown in FIG. 17. The difference spectrum $S_{OLD}$ in the conventional method was determined by the following equation (7):

$$S_{OLD}=(T_{Ref}-T_{Sam})/(T_{Ref}+T_{Sam}) \quad (7)$$

Comparison Between Example 1 and Comparative Example 1

Figure 18:
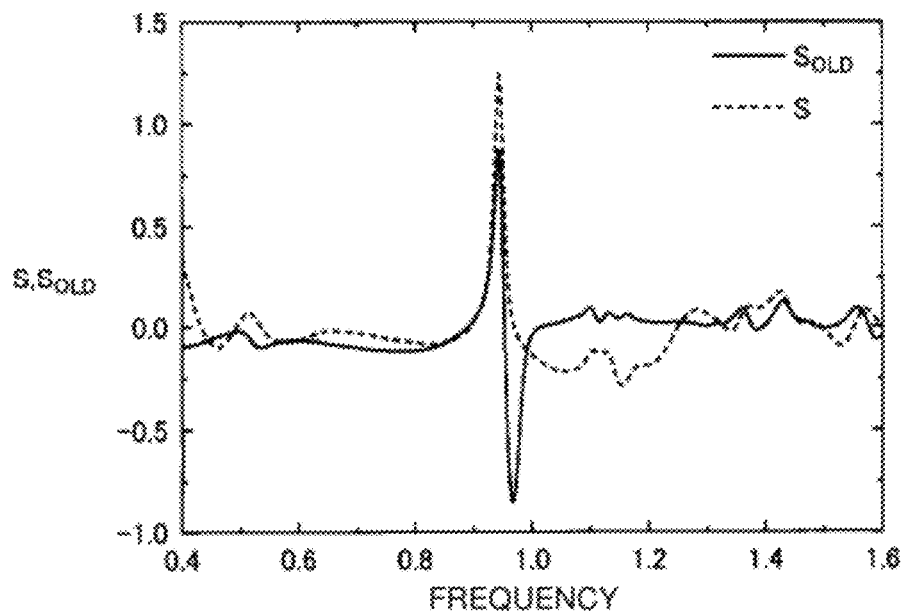
FIG. 18 is a graph showing both the difference spectrum S in Example 1 (see FIG. 15) and the difference spectrum $S_{OLD}$ in Comparative Example 1 (see FIG. 17).

For comparison between the difference spectrum S in Example 1 (see FIG. 15) and the difference spectrum $S_{OLD}$ in Comparative Example 1 (see FIG. 17), both the spectra are shown in FIG. 18. As shown in FIG. 18, a positive peak waveform appears at around 0.93 THz in both the difference spectrum S in Example 1 and the difference spectrum $S_{OLD}$ in Comparative Example 1. This shows that in the difference spectrum S obtained in Example 1, an object can be measured in the same manner as in the case of the difference spectrum $S_{OLD}$ obtained in the conventional method (Comparative Example 1), and that the peak value in Example 1 is higher than that in Comparative Example 1.

Example 2

In the same manner as in Example 1 except that dielectric films having thicknesses of 5 μm, 10 μm, and 20 μm were used, a simulation calculation of frequency characteristics was performed using an electromagnetic field simulator, MicroStripes (made by CST AG).

Figure 19:
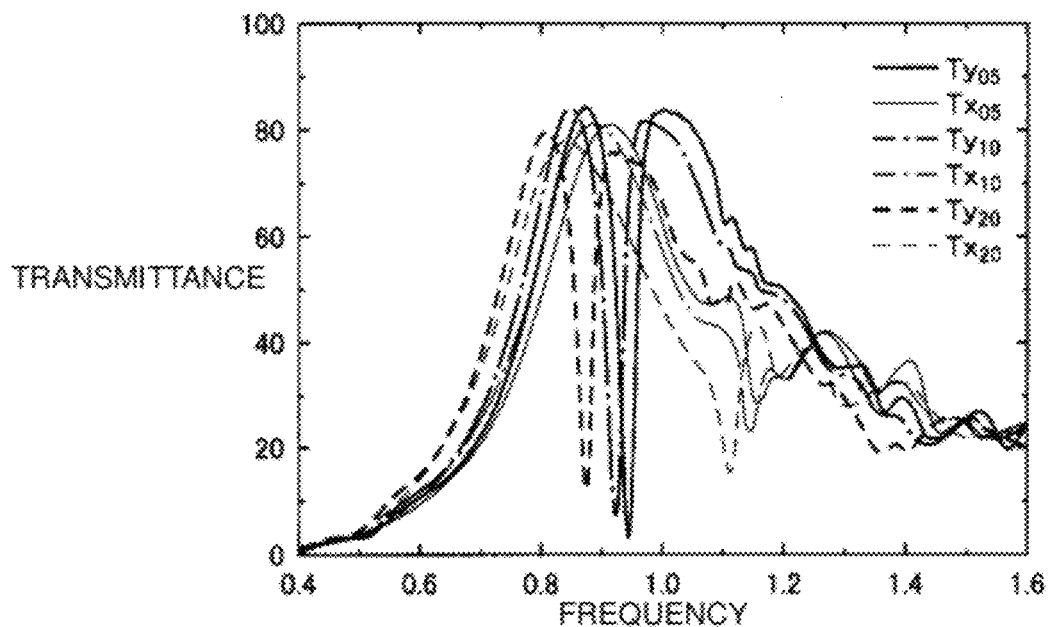
FIG. 19 is a graph showing transmittance spectra under various conditions in Example 2.

FIG. 19 shows Ty (first frequency characteristic) and Tx (second frequency characteristic) calculated for each of dielectric films having thicknesses of 5 μm, 10 μm, and 20 μm. In FIG. 19, Ty and Tx obtained in the case of using the dielectric film 5 μm thick are represented by $Ty_{05}$ and $Tx_{05}$, Ty and Tx obtained in the case of using the dielectric film 10 μm thick are represented by $Ty_{10}$ and $Tx_{10}$, and Ty and Tx obtained in the case of using the dielectric film 20 μm thick are represented by $Ty_{20}$ and $Tx_{20}$.

Figure 20:
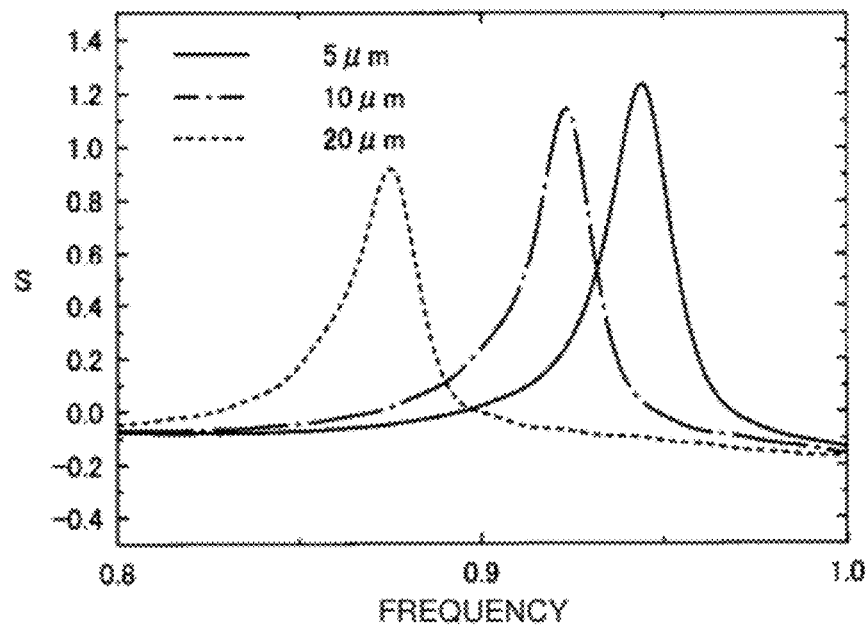
FIG. 20 is a graph showing a difference spectrum S in the case of using each of dielectric films having thicknesses of 5 μm ($Ty_{05}$ and $Tx_{05}$), 10 μm ($Ty_{10}$ and $Tx_{10}$), and 20 μm ($Ty_{20}$ and $Tx_{20}$) in the transmittance spectra shown in FIG. 19.

FIG. 20 shows a difference spectrum between the transmittance spectrum (Ty) of the first electromagnetic wave and the transmittance spectrum (Tx) of the second electromagnetic wave in the case of using each of the dielectric films having thicknesses of 5 μm, 10 μm, and 20 μm in FIG. 19 (i.e., a difference spectrum S between $Ty_{05}$ and $Tx_{05}$, a difference spectrum S between $Ty_{10}$ and $Tx_{10}$, and a difference spectrum S between $Ty_{20}$ and $Tx_{20}$ in FIG. 19). Each of the difference spectra S was determined by equation (6) described above. FIG. 20 shows that the peak value and the peak position with respect to the frequency on the horizontal axis vary depending on the thickness of the dielectric film (or the quantity of the object).

Figure 21:
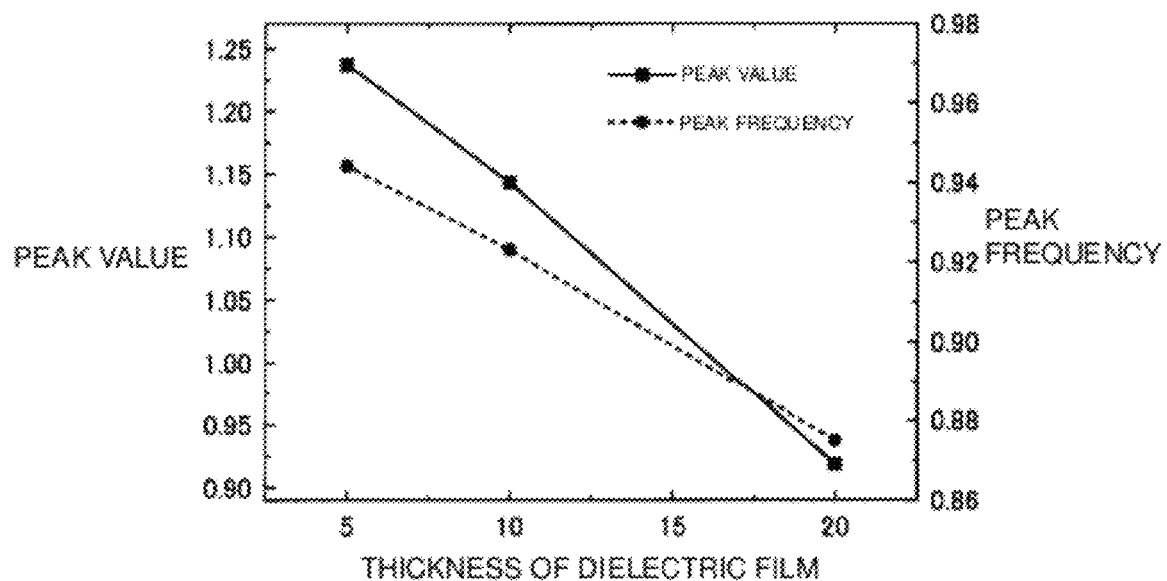
FIG. 21 is a graph in which the thicknesses of the dielectric films in FIG. 20 are plotted on the horizontal axis, and peak values and peak frequencies in the difference spectra in FIG. 20 are plotted on the vertical axis.

FIG. 21 is a graph in which the thicknesses of the dielectric films in FIG. 20 are plotted on the horizontal axis, and peak values and peak frequencies in the difference spectra in FIG. 20 are plotted on the vertical axis. FIG. 21 shows that a calibration curve for determining the quantity of an object can be obtained from the relationship between the thickness of the dielectric film (or the quantity of the object) and the peak value of the difference spectrum, or the relationship between the thickness of the dielectric film (or the quantity of the object) and the peak frequency of the difference spectrum.

Example 3

In the same manner as in Example 1 except that dielectric films having a dielectric loss tangent of 0.01 and thicknesses of 0 nm (no film), 100 nm, 200 nm, and 300 nm were used, a simulation calculation of frequency characteristics was performed using an electromagnetic field simulator, MicroStripes (made by CST AG).

Figure 22:
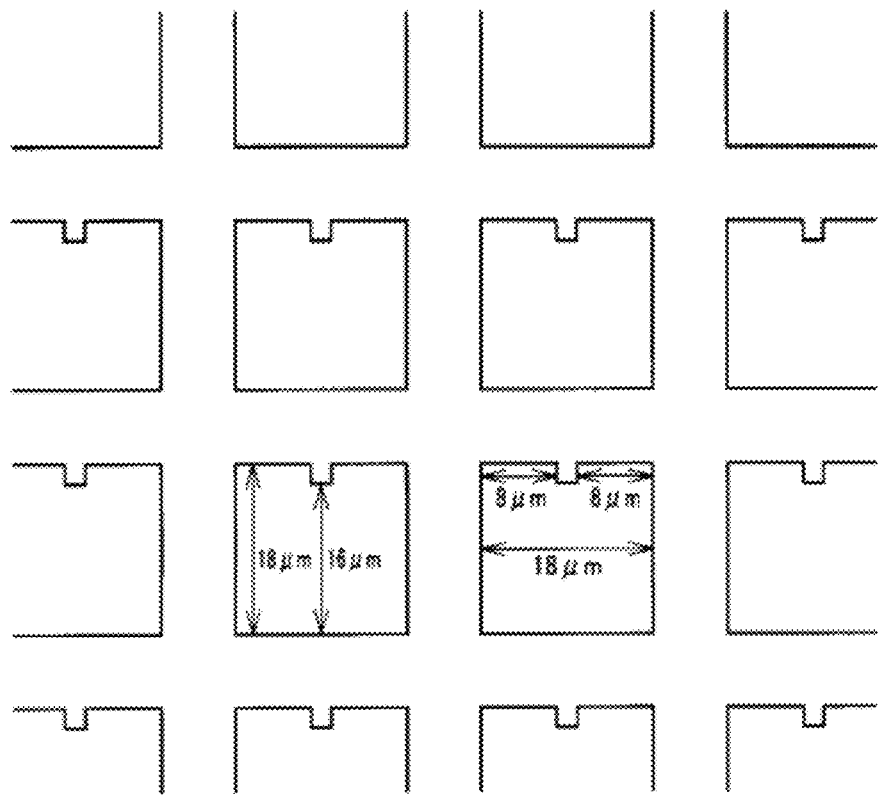
FIG. 22 illustrates a shape of openings of a metal mesh used in Example 3.

A metal mesh, such as that illustrated in FIG. 22, was used as a model. As illustrated, the metal mesh has void portions (of 18-μm-square) each of which is provided with a 2-μm-square protrusion at the center of one side. The metal mesh is 26 μm in grid spacing ("s" in FIG. 2(b)), 6 μm in thickness, and 0.13-mm-square plate-like in overall shape. The distance between the port 31 (see FIG. 12) and the center of gravity of the metal mesh 1 was set to 23 μm, and the distance between the port 32 (see FIG. 12) and the center of gravity of the metal mesh 1 was set to 23 μm. The ports 31 and 32 each are a 6-μm-thick plate having a 0.13-mm-square principal surface.

Figure 23:
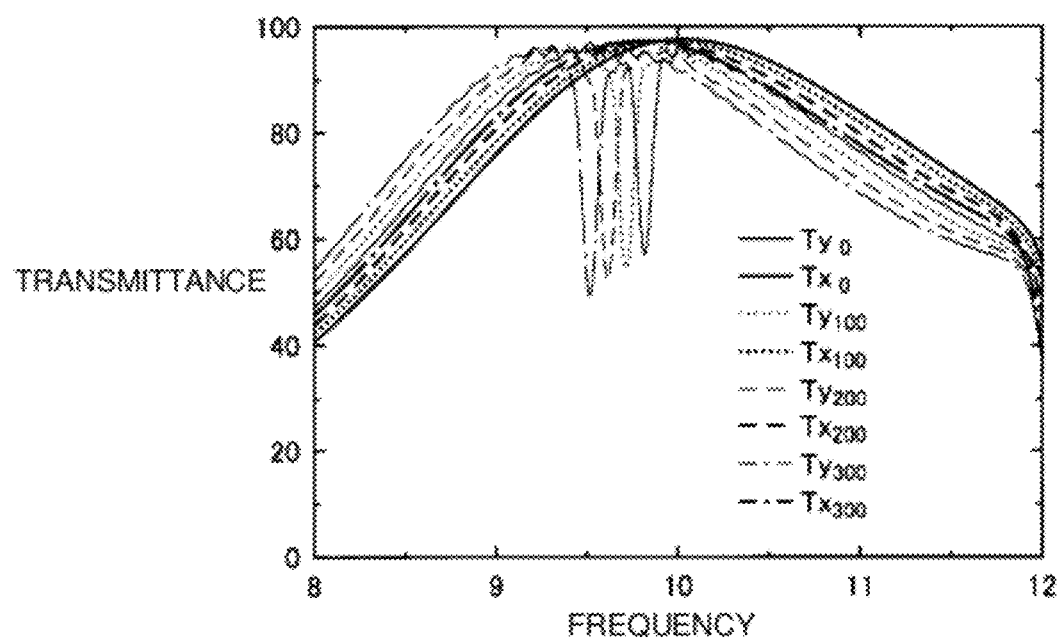
FIG. 23 is a graph showing transmittance spectra under various conditions in Example 3.

FIG. 23 shows Ty and Tx calculated for each of the dielectric films having thicknesses of 0 nm, 100 nm, 200 nm, and 300 nm. In FIG. 23, Ty and Tx obtained in the case of using the dielectric film 0 nm thick (or in the case of using no dielectric film) are represented by $Ty_0$ and $Tx_0$, Ty and Tx obtained in the case of using the dielectric film 100 nm thick are represented by $Ty_{100}$ and $Tx_{100}$, Ty and Tx obtained in the case of using the dielectric film 200 nm thick are represented by $Ty_{200}$ and $Tx_{200}$, and Ty and Tx obtained in the case of using the dielectric film 300 nm thick are represented by $Ty_{300}$ and $Tx_{300}$.

Figure 24:
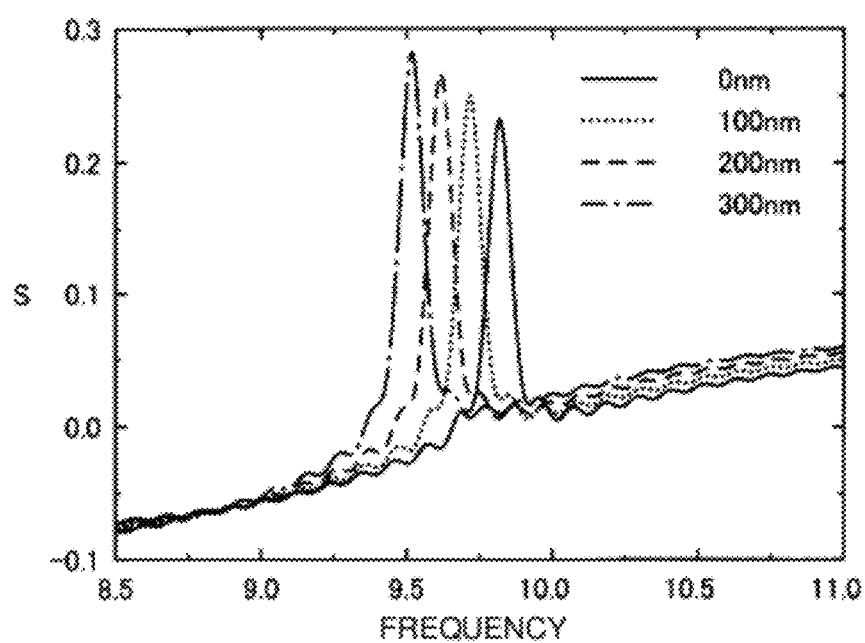
FIG. 24 is a graph showing a difference spectrum S in the case of using each of dielectric films having thicknesses of 0 nm ($Ty_0$ and $Tx_0$), 100 nm ($Ty_{100}$ and $Tx_{100}$), 200 nm ($Ty_{200}$ and $Tx_{200}$), and 300 nm ($Ty_{300}$ and $Tx_{300}$) in the transmittance spectra shown in FIG. 23.

FIG. 24 shows a difference spectrum between the transmittance spectrum of the first electromagnetic wave and the transmittance spectrum of the second electromagnetic wave in the case of using each of the dielectric films having thicknesses of 0 nm, 100 nm, 200 nm, and 300 nm in FIG. 23. Each of the difference spectra S was determined by equation (6) described above. FIG. 24 shows that the peak value and the peak position with respect to the frequency on the horizontal axis vary depending on the thickness of the dielectric film (or the quantity of the object).

Figure 25:
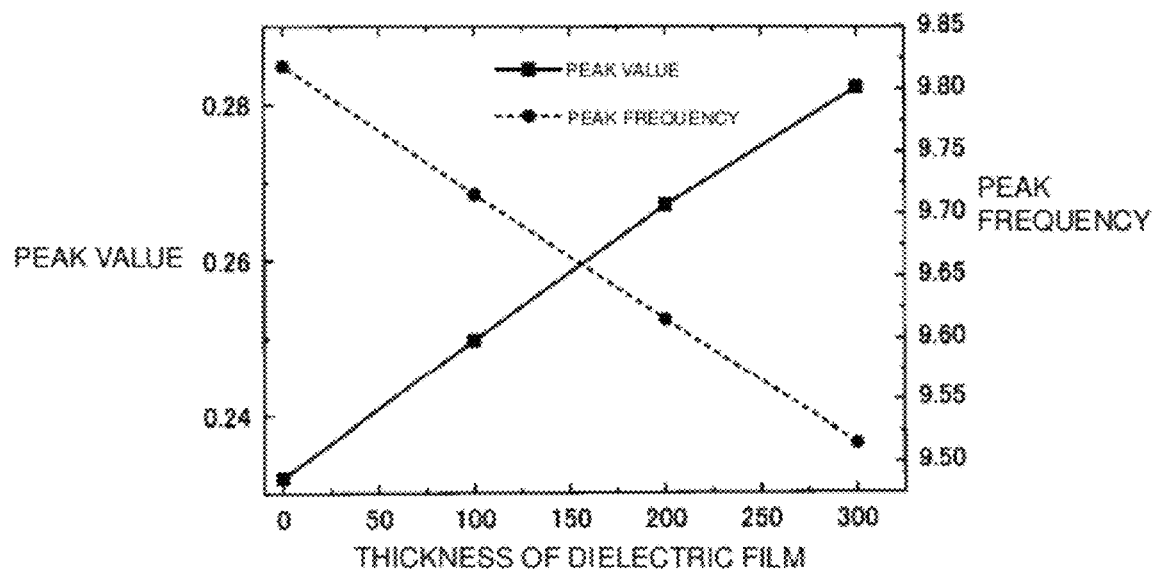
FIG. 25 is a graph in which the thicknesses of the dielectric films in FIG. 24 are plotted on the horizontal axis, and peak values and peak frequencies in the difference spectra in FIG. 24 are plotted on the vertical axis.

FIG. 25 is a graph in which the thicknesses of the dielectric films in FIG. 24 are plotted on the horizontal axis, and peak values and peak frequencies in the difference spectra in FIG. 24 are plotted on the vertical axis. FIG. 25 shows that a calibration curve for determining the quantity of an object can be obtained from the relationship between the thickness of the dielectric film (or the quantity of the object) and the peak value of the difference spectrum, or the relationship between the thickness of the dielectric film (or the quantity of the object) and the peak frequency of the difference spectrum.

Example 4

In the present example, a simulation calculation was performed for examining the effect of variation in dimension (opening size) of a metal mesh on measurement.

In the same manner as in Example 1 except that two types of metal meshes were used, which are metal mesh-1 and metal mesh-2 having opening sizes ("d" in FIG. 2(b)) of 180 μm and 184 μm, respectively, a simulation calculation of frequency characteristics was performed using an electromagnetic field simulator, MicroStripes (made by CST AG). There is mathematically a 2.2% difference in opening size between metal mesh-1 and metal mesh-2. In the simulation calculation of the present example, the frequency characteristics (first frequency characteristic and second frequency characteristic) of electromagnetic waves transmitted through these metal meshes were calculated for two types of electromagnetic waves, an electromagnetic wave polarized in the Y-axis direction (first electromagnetic wave) and an electromagnetic wave polarized in the X-axis direction (second electromagnetic wave).

Figure 26:
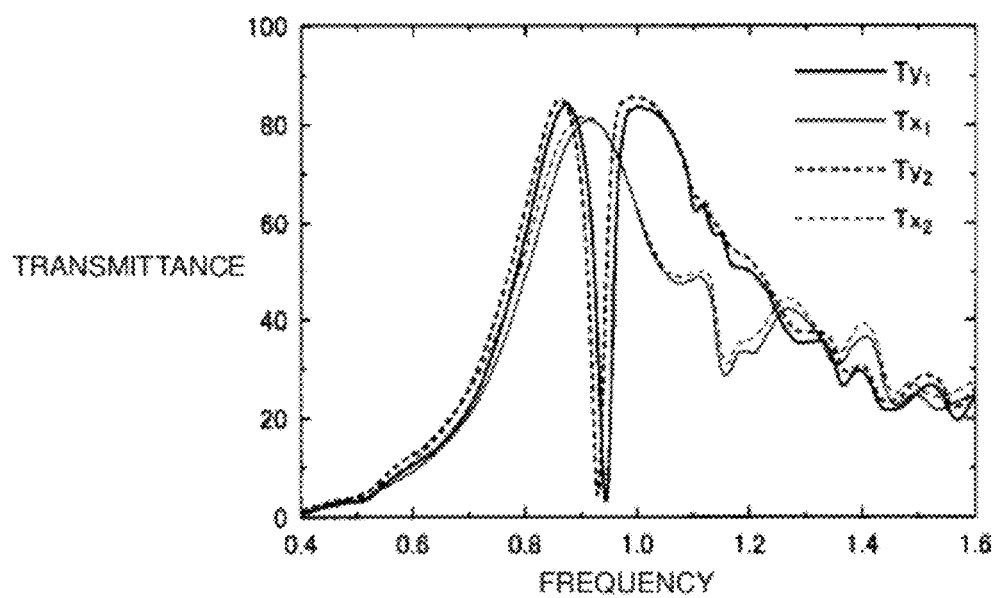
FIG. 26 is a graph showing each transmittance spectrum in Example 4.

FIG. 26 shows a transmittance spectrum of the electromagnetic wave polarized in the Y-axis direction (first electromagnetic wave) and a transmittance spectrum of the electromagnetic wave polarized in the X-axis direction (second electromagnetic wave) calculated for each of metal mesh-1 (opening size: 180 μm) and metal mesh-2 (opening size: 184 μm). In FIG. 26, Ty and Tx obtained in the case of using the metal mesh with an opening size of 180 μm are represented by $Ty_1$ and $Tx_1$, and Ty and Tx obtained in the case of using the metal mesh with an opening size of 184 μm are represented by $Ty_2$ and $Tx_2$.

A comparison in FIG. 26 reveals that even if the object (dielectric film) is the same, the frequency characteristic obtained when the object is provided varies depending on the frequency characteristic (or opening size) of the metal mesh. Such variation in the opening size of the metal mesh may occur as an error in the process of making the metal mesh, and such an error in opening size may lead to an error in measurement. However, by determining a difference spectrum S, it is possible to solve the problem of measurement error caused by an error of the metal mesh, such as an error in opening size.

Figure 27:
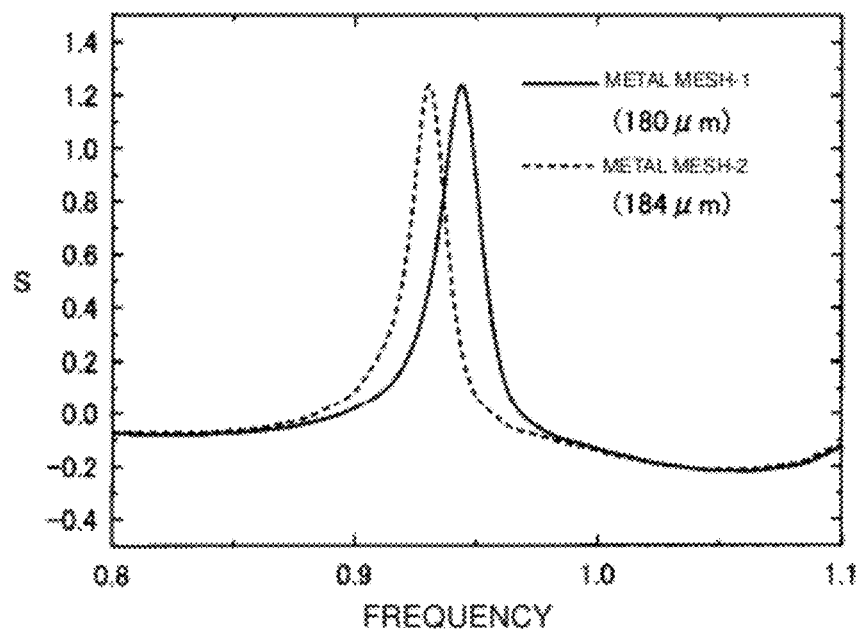
FIG. 27 is a graph showing a difference spectrum S in the case of using each of metal mesh-1 ($Ty_1$ and $Tx_1$) and metal mesh-2 ($Ty_2$ and $Tx_2$) in the transmittance spectra shown in FIG. 26.

FIG. 27 shows a difference spectrum S between the transmittance spectrum of the first electromagnetic wave and the transmittance spectrum of the second electromagnetic wave obtained in the case of using each of metal mesh-1 and metal mesh-2 in FIG. 26. The difference spectrum S was determined by equation (6) described above. As shown in FIG. 27, when the object is the same, even if the peak frequency of the difference spectrum S varies depending on the frequency characteristic (opening size) of the metal mesh, the peak value of the difference spectrum S is the same. Therefore, when the quantity of the object is determined on the basis of the peak value of the difference spectrum, it is possible to eliminate the effect of variations in frequency characteristic (e.g., variations in opening size, grid spacing, thickness, and overall shape) caused by errors in manufacturing the void-arranged structure.

Comparative Example 2

A simulation calculation was performed for examining the effect of variation in dimension (opening size) of the metal mesh in a conventional measuring method.

Two metal meshes-1 (opening size: 180 μm) and one metal mesh-2 (opening size: 184 μm) were prepared, which are the same as those used in Example 4. A dielectric film which is the same as that used in Example 1 was firmly attached to each of the principal surfaces of one metal mesh-1 and one metal mesh-2.

As in Comparative Example 1, the polarization direction of an electromagnetic wave applied to a metal mesh was set only to the Y-axis direction in FIG. 12, and the polarization direction of an electromagnetic wave detected at the ports 31 and 32 was also set to the Y-axis direction. Then, a simulation calculation of frequency characteristics was performed using an electromagnetic field simulator, MicroStripes (made by CST AG).

First, a calculation was made to determine a frequency characteristic (background 1: $Back_R$) obtained when nothing was placed in the sample unit in FIG. 13 and a frequency characteristic (Ref) obtained when only metal mesh-1 was placed in the sample unit in FIG. 13. Then, Ref was divided by $Back_R$ to determine a transmittance spectrum in the case where only metal mesh-1 was placed. The calculated transmittance spectrum is shown as $T_{Ref}$ in FIG. 28.

Similarly, a calculation was made to determine a frequency characteristic (background 2: $Back_{S1}$) obtained when nothing was placed in the sample unit in FIG. 13 and a frequency characteristic (Sam1) obtained when metal mesh-1 with a dielectric film firmly attached thereto was placed in the sample unit in FIG. 13. Then, Sam1 was divided by $Back_{S1}$ to determine a transmittance spectrum of metal mesh-1 with the dielectric film firmly attached thereto. The calculated transmittance spectrum is shown as $T_{Sam1}$ in FIG. 28.

Similarly, a calculation was made to determine a frequency characteristic (background 3: $Back_{S2}$) obtained when nothing was placed in the sample unit in FIG. 13 and a frequency characteristic (Sam2) obtained when metal mesh-2 with a dielectric film firmly attached thereto was placed in the sample unit in FIG. 13. Then, Sam2 was divided by $Back_{S2}$ to determine a transmittance spectrum of metal mesh-2 with the dielectric film firmly attached thereto. The calculated transmittance spectrum is shown as $T_{Sam2}$ in FIG. 28.

Figure 28:
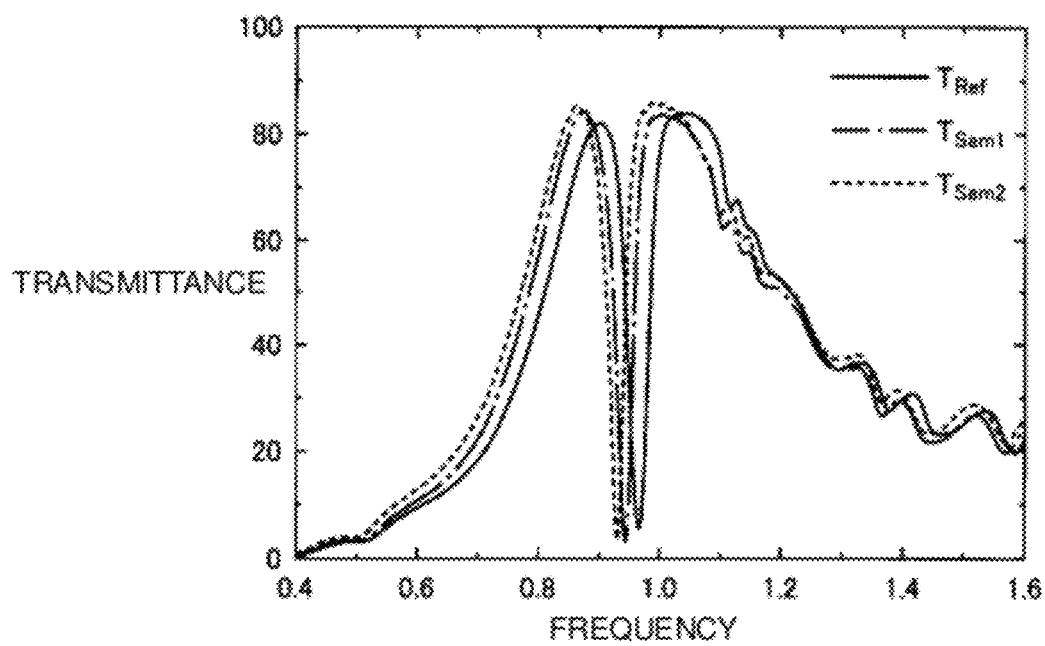
FIG. 28 is a graph showing each transmittance spectrum in Comparative Example 2.

A comparison between $T_{Sam1}$ and $T_{Sam2}$ in FIG. 28 reveals that even if the object is the same, the frequency characteristic obtained when the object is provided varies depending on the frequency characteristic (opening size) of the metal mesh.

Figure 29:
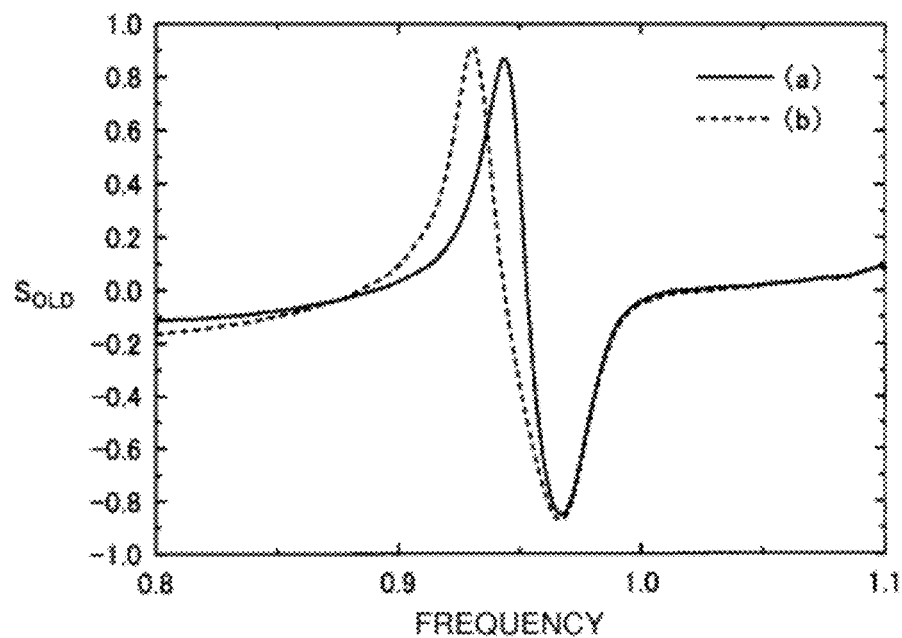
FIG. 29 is a graph showing a difference spectrum $S_{OLD}$ between $T_{Ref}$ and $T_{Sam1}$ and a difference spectrum $S_{OLD}$ between $T_{Ref}$ and $T_{Sam2}$ in the transmittance spectra shown in FIG. 28.

A difference spectrum $S_{OLD}$ between $T_{Ref}$ and $T_{Sam1}$ in the conventional method in FIG. 28 is shown as (a) in FIG. 29. A difference spectrum $S_{OLD}$ between $T_{Ref}$ and $T_{Sam2}$ in the conventional method in FIG. 28 is shown as (b) in FIG. 29. The difference spectrum $S_{OLD}$ in the conventional method was determined by equation (7) described above. As shown in FIG. 29, even if the object is the same, the frequency characteristic obtained when the object is provided varies in terms of both the peak frequency and the peak value, depending on the frequency characteristic (opening size) of the metal mesh.

Example 5

In the present example, a simulation calculation was performed on the assumption of the apparatus configuration of Embodiment 3 described with reference to FIG. 6. In the present example, one type of electromagnetic wave was applied to the void-arranged structure. The electromagnetic wave propagated in the Z-axis direction (see FIGS. 7(a), 7(b), 8(a) and 8(b)) and was polarized in the Y-axis direction (see FIGS. 7(a), 7(b), 8(a) and 8(b)). The polarization direction of the electromagnetic wave detected at each port was set to the Y-axis direction (see FIG. 12).

Then, a transmittance spectrum (Tv) obtained when the void-arranged structure was placed, as illustrated in FIGS. 7(a) and 7(b), such that the principal surface of the metal mesh was perpendicular to the propagation direction of the electromagnetic wave was defined as a second frequency characteristic. On the other hand, a transmittance spectrum (Tt) obtained when the void-arranged structure was placed, as illustrated in FIGS. 8(a) and 8(b), by being rotated from the position of FIGS. 7(a) and 7(b) about the rotation axis 12 (X-axis) was defined as a first frequency characteristic. The rotation angle θ of the void-arranged structure was set to 9°.

In the same manner as in Example 1 except for the conditions described above, a simulation calculation of frequency characteristics was performed using a metal mesh and an object same as those of Example 1 as a model.

Figure 30:
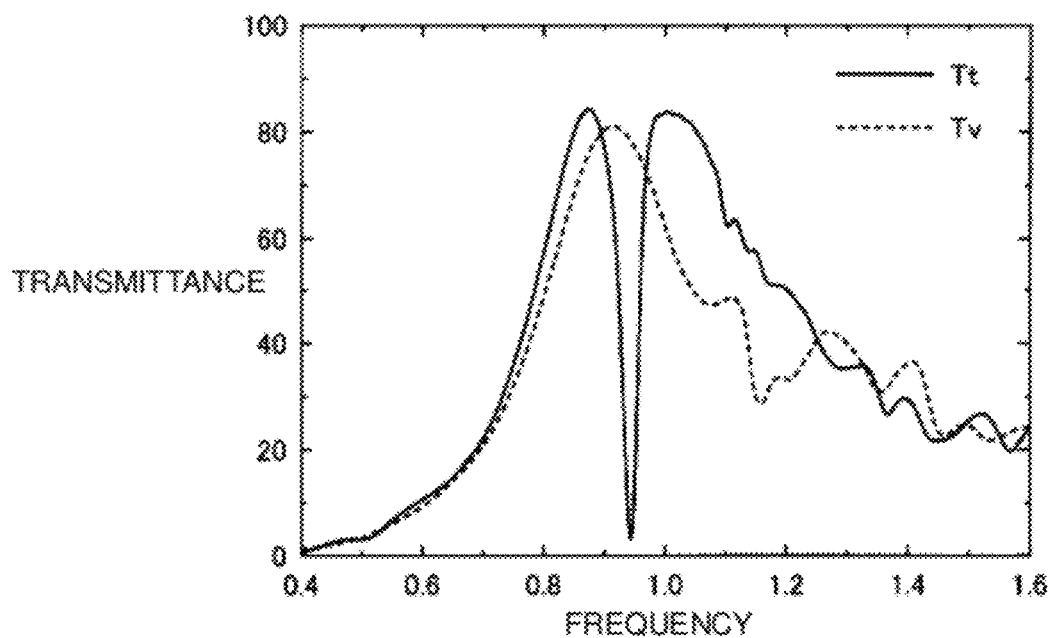
FIG. 30 is a graph showing a transmittance spectrum Tt and a transmittance spectrum Tv in Example 5.
Figure 31:
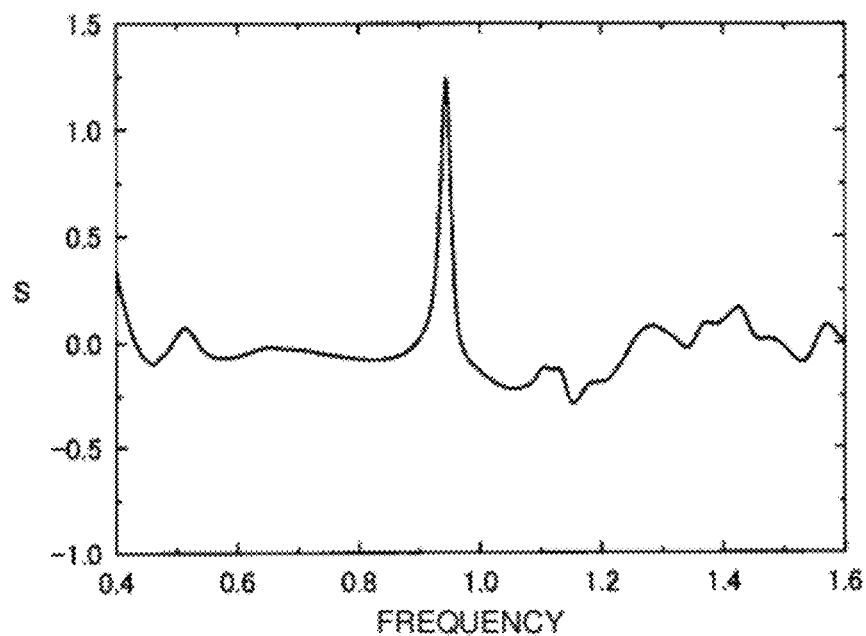
FIG. 31 is a graph showing a difference spectrum S in Example 5.

FIG. 30 shows calculated Tt and Tv. FIG. 31 shows a difference spectrum S between Tt and Tv in FIG. 30. The difference spectrum S was determined by the following equation (6') obtained by substituting a=0.97, b=−0.97, c=0.696, and d=1.304 into equation (1') described above:

$$S=\{0.97Tv-0.97Tt)\}/\{0.696Tv+1.304Tt)\} \quad (6')$$

A positive peak appearing at around 0.93 THz in FIG. 31 represents characteristics of the object. For example, after S(ν) is measured for various quantities of the object in advance, peak values of S(ν) are determined to obtain a calibration curve, and then a value obtained as a result of actual measurement is compared with the calibration curve. It is thus possible to calculate the quantity of the object.

Figure 32:
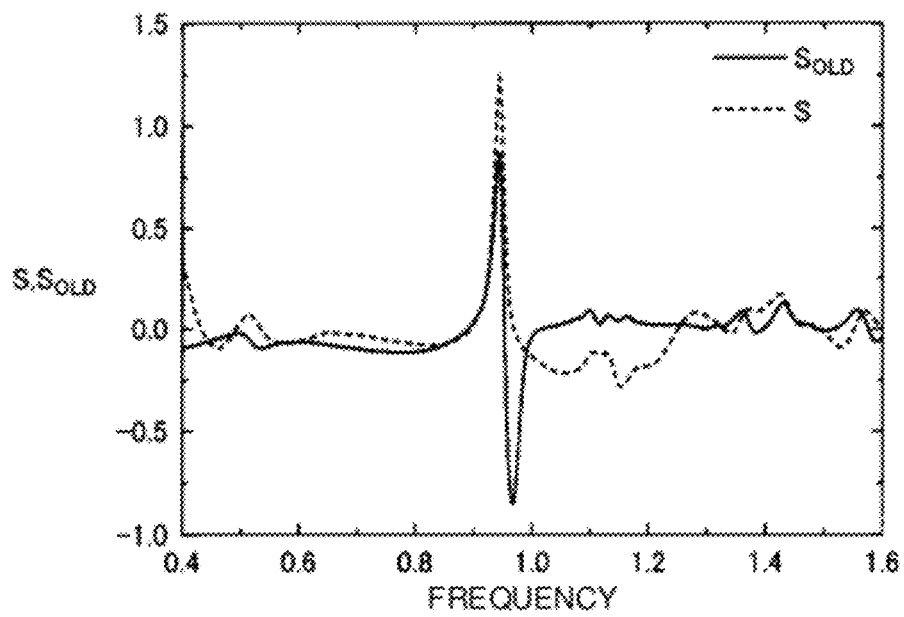
FIG. 32 is a graph showing both the difference spectrum S in Example 5 (see FIG. 31) and the difference spectrum $S_{OLD}$ in Comparative Example 1 (see FIG. 17).

For comparison between the difference spectrum S in Example 5 (see FIG. 31) and the difference spectrum $S_{OLD}$ in Comparative Example 1 (see FIG. 17), both the spectra are shown in FIG. 32. As shown in FIG. 32, a positive peak waveform appears at around 0.93 THz in both the difference spectrum S in Example 5 and the difference spectrum $S_{OLD}$ in Comparative Example 1. This shows that in the difference spectrum S obtained in Example 5, an object can be measured in the same manner as in the case of the difference spectrum $S_{OLD}$ obtained in the conventional method (Comparative Example 1), and that the peak value in Example 5 is higher than that in Comparative Example 1.

Example 6

In the same manner as in Example 5 except that dielectric films having thicknesses of 5 µm, 10 µm, and 20 µm were used, a simulation calculation of frequency characteristics was performed using an electromagnetic field simulator, MicroStripes (made by CST AG).

Figure 33:
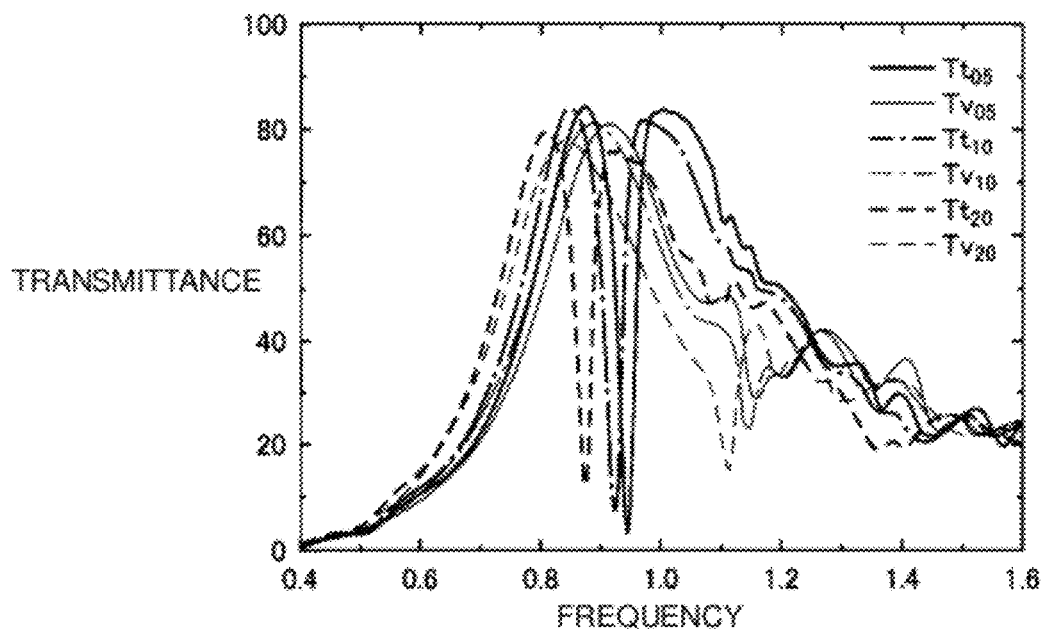
FIG. 33 is a graph showing transmittance spectra under various conditions in Example 6.

FIG. 33 shows Tt and Tv calculated for each of the dielectric films having thicknesses of 5 µm, 10 µm, and 20 µm. In FIG. 33, Tt and Tv obtained in the case of using the dielectric film 5 µm thick are represented by $Tt_{05}$ and $Tv_{05}$, Tt and Tv obtained in the case of using the dielectric film 10 µm thick are represented by $Tt_{10}$ and $Tv_{10}$, and Tt and Tv obtained in the case of using the dielectric film 20 µm thick are represented by $Tt_{20}$ and $Tv_{20}$.

Figure 34:
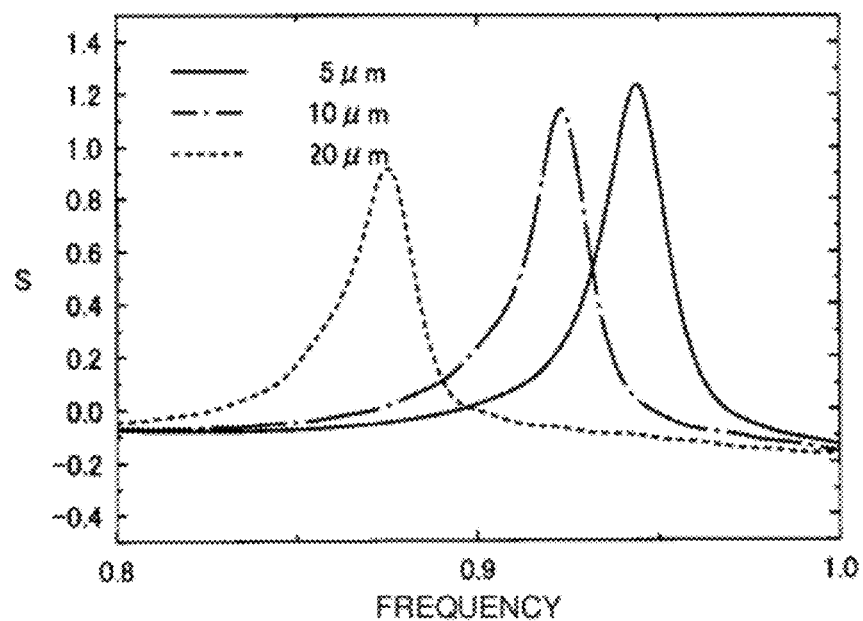
FIG. 34 is a graph showing a difference spectrum S in the case of using each of dielectric films having thicknesses of 5 μm ($Tt_{05}$ and $Tv_{05}$), 10 μm ($Tt_{10}$ and $Tv_{10}$), and 20 μm ($Tt_{20}$ and $Tv_{20}$) in the transmittance spectra shown in FIG. 33.

FIG. 34 shows a difference spectrum between Tt and Tv in the case of using each of the dielectric films having thicknesses of 5 µm, 10 µm, and 20 µm in FIG. 33 (i.e., a difference spectrum S between $Tt_{05}$ and $Tv_{05}$, a difference spectrum S between $Tt_{10}$ and $Tv_{10}$, and a difference spectrum S between $Tt_{20}$ and $Tv_{20}$ in FIG. 33). Each of the difference spectra S was determined by equation (6') described above. FIG. 34 shows that the peak value and the peak position with respect to the frequency on the horizontal axis vary depending on the thickness of the dielectric film (or the quantity of the object).

Figure 35:
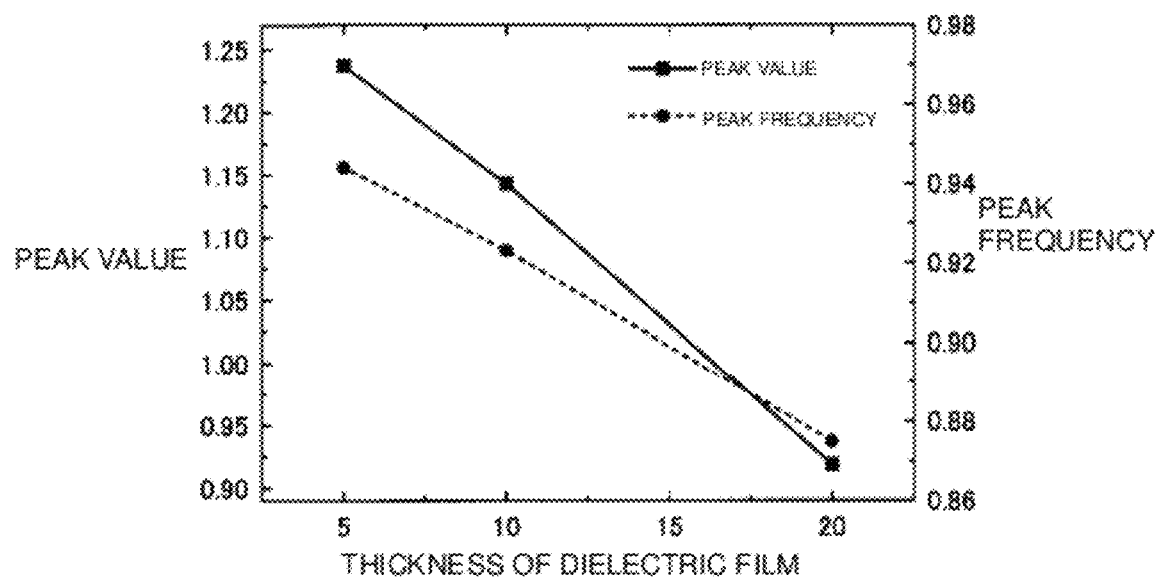
FIG. 35 is a graph in which the thicknesses of the dielectric films in FIG. 34 are plotted on the horizontal axis, and peak values and peak frequencies in the difference spectra in FIG. 34 are plotted on the vertical axis.

FIG. 35 is a graph in which the thicknesses of the dielectric films in FIG. 34 are plotted on the horizontal axis, and peak values and peak frequencies in the difference spectra in FIG. 34 are plotted on the vertical axis. FIG. 35 shows that a calibration curve for determining the quantity of an object can be obtained from the relationship between the thickness of the dielectric film (or the thickness of the object) and the peak value of the difference spectrum, or the relationship between the thickness of the dielectric film (or the thickness of the object) and the peak frequency of the difference spectrum.

Example 7

In the same manner as in Example 5 except that dielectric films having a dielectric loss tangent of 0.01 and thicknesses of 0 nm (no film), 100 nm, 200 nm, and 300 nm were used, a simulation calculation of frequency characteristics was performed using an electromagnetic field simulator, MicroStripes (made by CST AG).

A metal mesh, such as that illustrated in FIG. 22, was used as a model. As illustrated, the metal mesh has void portions each of which is provided with a protrusion. The metal mesh is 26 µm in grid spacing ("s" in FIG. 2(b)), 6 µm in thickness, and 0.13-mm-square plate-like in overall shape. The distance between the port 31 (see FIG. 12) and the center of gravity of the metal mesh 1 was set to 23 µm, and the distance between the port 32 (see FIG. 12) and the center of gravity of the metal mesh 1 was set to 23 µm. The ports 31 and 32 each are a 6-µm-thick plate having a 0.13-mm-square principal surface.

Figure 36:
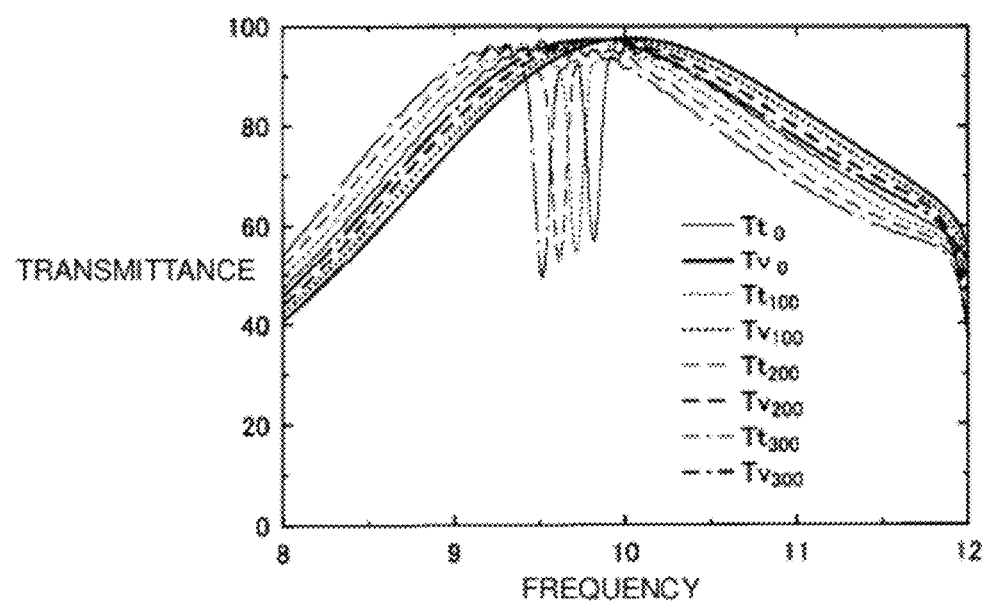
FIG. 36 is a graph showing transmittance spectra under various conditions in Example 7.

FIG. 36 shows Tt and Tv calculated for each of the dielectric films having thicknesses of 0 nm, 100 nm, 200 nm, and 300 nm. In FIG. 36, Tt and Tv obtained in the case of using the dielectric film 0 nm thick (or in the case of using no dielectric film) are represented by $Tt_0$ and $Tv_0$, Tt and Tv obtained in the case of using the dielectric film 100 nm thick are represented by $Tt_{100}$ and $Tv_{100}$, Tt and Tv obtained in the case of using the dielectric film 200 nm thick are represented by $Tt_{200}$ and $Tv_{200}$, and Tt and Tv obtained in the case of using the dielectric film 300 nm thick are represented by $Tt_{300}$ and $Tv_{300}$.

Figure 37:
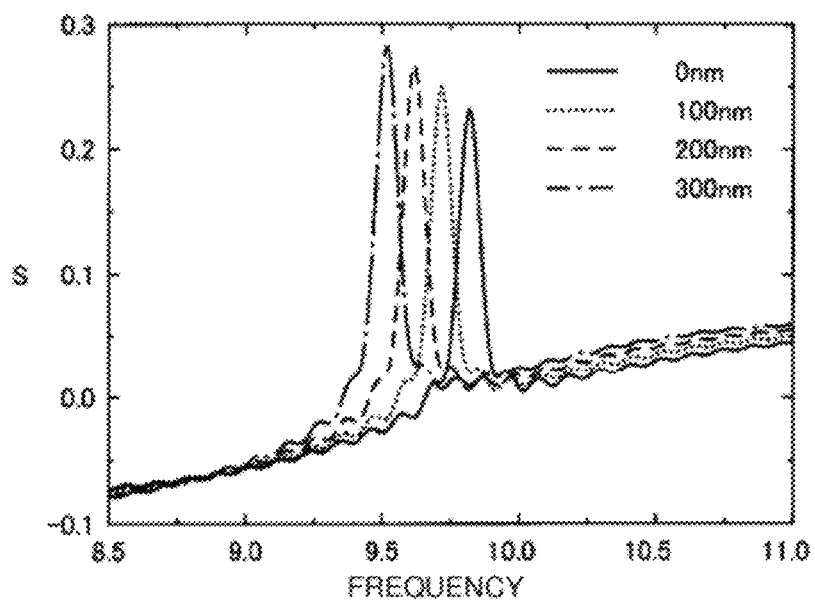
FIG. 37 is a graph showing a difference spectrum S in the case of using each of dielectric films having thicknesses of 0 nm ($Tt_0$ and $Tv_0$), 100 nm ($Tt_{100}$ and $Tv_{100}$), 200 nm ($Tt_{200}$ and $Tv_{200}$), and 300 nm ($Tt_{300}$ and $Tv_{300}$) in the transmittance spectra shown in FIG. 36.

FIG. 37 shows a difference spectrum between Tt and Tv in the case of using each of the dielectric films having thicknesses of 0 nm, 100 nm, 200 nm, and 300 nm in FIG. 36. Each of the difference spectra S was determined by equation (6') described above. FIG. 37 shows that the peak value and the peak position with respect to the frequency on the horizontal axis vary depending on the thickness of the dielectric film (or the quantity of the object).

Figure 38:
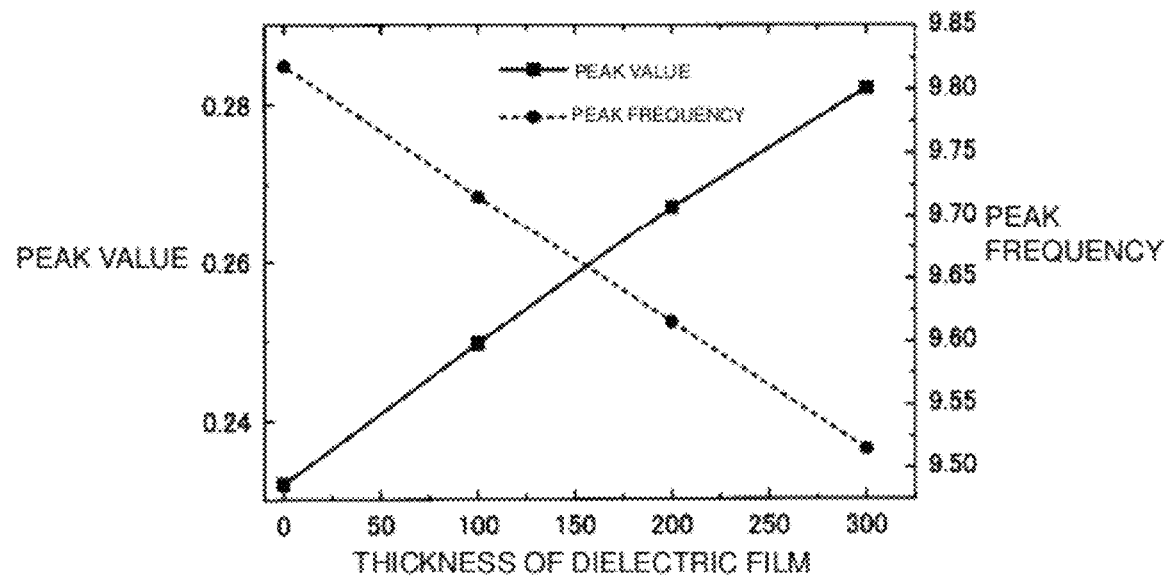
FIG. 38 is a graph in which the thicknesses of the dielectric films in FIG. 37 are plotted on the horizontal axis, and peak values and peak frequencies in the difference spectra in FIG. 37 are plotted on the vertical axis.

FIG. 38 is a graph in which the thicknesses of the dielectric films in FIG. 37 are plotted on the horizontal axis and peak values and peak frequencies in the difference spectra in FIG. 37 are plotted on the vertical axis. FIG. 38 shows that a calibration curve for determining the quantity of an object can be obtained from the relationship between the thickness of the dielectric film (or the quantity of the object) and the peak value of the difference spectrum, or the relationship between the thickness of the dielectric film (or the quantity of the object) and the peak frequency of the difference spectrum.

Example 8

In the present example, a simulation calculation was performed for examining the effect of variation in dimension (opening size) of a metal mesh on measurement.

In the same manner as in Example 5 except that two types of metal meshes were used, which are metal mesh-1 and metal mesh-2 having opening sizes ("d" in FIG. 2(b)) of 180 µm and 184 µm, respectively, a simulation calculation of frequency characteristics was performed using an electromagnetic field simulator, MicroStripes (made by CST AG). There is mathematically a 2.2% difference in opening size between metal mesh-1 and metal mesh-2.

Figure 39:
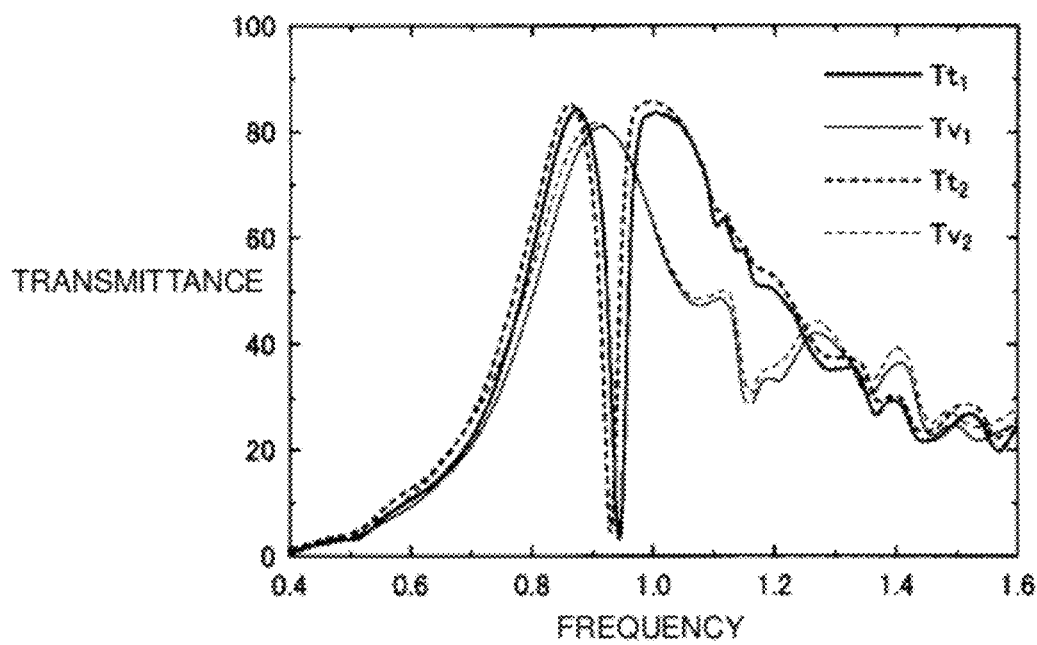
FIG. 39 is a graph showing each transmittance spectrum in Example 8.

FIG. 39 shows Tt and Tv calculated for each of metal mesh-1 (opening size: 180 µm) and metal mesh-2 (opening size: 184 µm). In FIG. 39, Tt and Tv obtained in the case of using the metal mesh having an opening size of 180 µm are represented by $Tt_1$ and $Tv_1$, and Tt and Tv obtained in the case of using the metal mesh having an opening size of 184 μm are represented by $Tt_2$ and $Tv_2$.

A comparison in FIG. 39 reveals that even if the object (dielectric film) is the same, the frequency characteristic obtained when the object is provided varies depending on the frequency characteristic (or opening size) of the metal mesh. Such variation in the opening size of the metal mesh may occur as an error in the process of making the metal mesh, and such an error in opening size may lead to an error in measurement. However, by determining a difference spectrum S, it is possible to solve the problem of measurement error caused by an error of the metal mesh, such as an error in opening size.

Figure 40:
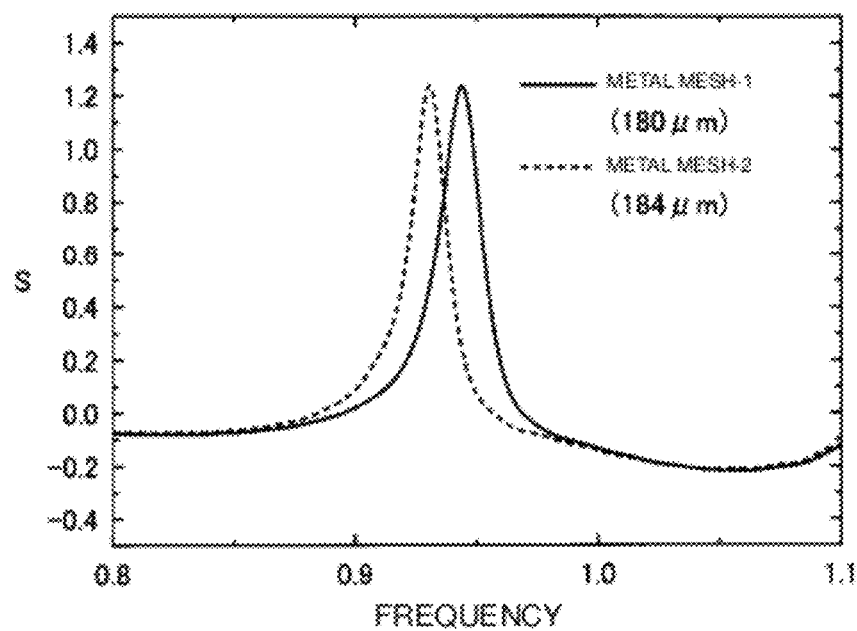
FIG. 40 is a graph showing a difference spectrum S in the case of using each of metal mesh-1 ($Tt_1$ and $Tv_1$) and metal mesh-2 ($Tt_2$ and $Tv_2$) in the transmittance spectra shown in FIG. 39.

FIG. 40 shows a difference spectrum S between Tt and Tv obtained in the case of using each of metal mesh-1 and metal mesh-2 in FIG. 39. The difference spectrum S was determined by equation (6') described above. As shown in FIG. 40, when the object is the same, even if the peak frequency of the difference spectrum S varies depending on the frequency characteristic (opening size) of the metal mesh, the peak value of the difference spectrum S is the same.

On the other hand, in Comparative Example 2 which is a conventional measuring method, as shown in FIG. 29, even when the object is the same, the frequency characteristic obtained when the object is provided varies depending on the frequency characteristic (e.g., opening size) of the void-arranged structure. In the measuring method of the present invention, it is possible to eliminate the effect of variations in frequency characteristic (e.g., variations in opening size, grid spacing, thickness, and overall shape) caused by errors in manufacturing the void-arranged structure.

The embodiments and examples disclosed herein are to be considered illustrative, not restrictive, in every respect. The scope of the present invention is defined not by the above description but by the appended claims, and is intended to include meanings equivalent to the claims and all changes made within the scope.

REFERENCE SIGNS LIST

1: void-arranged structure
10a: principal surface
10b: side face
11: void portion
11a: void-portion side face
12: rotation axis
2: measuring apparatus
21: electromagnetic-wave emitting unit
22: detecting unit
23: emission control unit
24: analysis processing unit
25: display unit
31, 32: port

The invention claimed is:

1. A measuring method for measuring characteristics of an object to be measured, the method comprising:
applying electromagnetic waves to a void-arranged structure on which the object is held to detect frequency characteristics of the electromagnetic waves transmitted through the void-arranged structure, the void-arranged structure having at least two void portions that pass through the void-arranged structure in a direction perpendicular to a principal surface thereof, and
wherein the void-arranged structure has a grid structure in which the void portions are periodically arranged in at least one direction on the principal surface of the void-arranged structure;
detecting a first frequency characteristic and a second frequency characteristic as the frequency characteristics, wherein the first frequency characteristic includes a dip waveform, and the second frequency characteristic includes no dip waveform or a dip waveform having a depth smaller than that of the dip waveform in the first frequency characteristic; and
measuring the characteristics of the object on the basis of a relationship between the first frequency characteristic and the second frequency characteristic.

2. The measuring method according to claim 1, wherein the characteristics of the object are measured using a difference spectrum S determined from the first frequency characteristic and the second frequency characteristic by an equation (1):

$$S = \frac{aTx + bTy}{cTx + dTy} \quad (1)$$

where Ty is a transmittance of an electromagnetic wave in the first frequency characteristic, Tx is a transmittance of an electromagnetic wave in the second frequency characteristic, and a, b, c, and d are independent constants.

3. The measuring method according to claim 2, wherein a quantity of the object is calculated by comparing a specific peak value of the difference spectrum S with a calibration curve generated on the basis of specific peak values of difference spectra S obtained by measuring various quantities of the object.

4. The measuring method according to claim 1, wherein the dip waveform in the first frequency characteristic is generated by TE11-mode resonance of the void-arranged structure.

5. The measuring method according to claim 1, wherein the electromagnetic waves are linearly polarized electromagnetic waves;
when the principal surface of the void-arranged structure is not parallel to a polarization direction of the electromagnetic waves, a frequency characteristic of an electromagnetic wave transmitted through the void-arranged structure is detected as the first frequency characteristic; and
when the principal surface of the void-arranged structure is parallel to the polarization direction of the electromagnetic waves, a frequency characteristic of an electromagnetic wave transmitted through the void-arranged structure is detected as the second frequency characteristic.

6. The measuring method according to claim 1, wherein a first electromagnetic wave and a second electromagnetic wave, which are linearly polarized electromagnetic waves, are applied to the void-arranged structure such that polarization directions thereof are different from each other; and
a frequency characteristic of the first electromagnetic wave transmitted through the void-arranged structure is detected as the first frequency characteristic, and a frequency characteristic of the second electromagnetic wave transmitted through the void-arranged structure is detected as the second frequency characteristic.

7. The measuring method according to claim 6, wherein the first electromagnetic wave and the second electromagnetic wave are applied to the void-arranged structure such that
a propagation direction of the first electromagnetic wave is the same as that of the second electromagnetic wave,
a polarization direction of the first electromagnetic wave is perpendicular to the propagation direction, and a polarization direction of the second electromagnetic wave is perpendicular to both the propagation direction and the polarization direction of the first electromagnetic wave.

8. The measuring method according to claim 7, wherein the void-arranged structure is formed as a periodic array of the void portions arranged in rows and columns in a square grid pattern; and the void-arranged structure is placed such that when being projected onto a plane perpendicular to the propagation direction, one of the row and column directions of the void portions coincides with the polarization direction of the first electromagnetic wave, and the other of the row and column directions coincides with the polarization direction of the second electromagnetic wave.

9. The measuring method according to claim 7, wherein the void-arranged structure is placed by being rotated from a position at which the principal surface thereof is perpendicular to the propagation direction by a given angle about a rotation axis passing through a center of gravity of the void-arranged structure and parallel to the polarization direction of the second electromagnetic wave.

10. The measuring method according to claim 1, wherein a frequency characteristic of the void-arranged structure obtained by applying the electromagnetic wave to the void-arranged structure in a predetermined first direction with respect to the principal surface of the void-arranged structure is detected as the first frequency characteristic; and a frequency characteristic of the void-arranged structure obtained by applying the electromagnetic wave to the void-arranged structure in a second direction different from the first direction with respect to the principal surface of the void-arranged structure is detected as the second frequency characteristic.

11. The measuring method according to claim 10, wherein the second direction is perpendicular to the principal surface of the void-arranged structure.

12. The measuring method according to claim 10, wherein the electromagnetic wave applied in the first direction and the electromagnetic wave applied in the second direction are linearly polarized electromagnetic waves.

13. The measuring method according to claim 12, wherein the void-arranged structure is formed by a periodic array of the void portions arranged in rows and columns in a square grid pattern; and when detecting the first frequency characteristic, the void-arranged structure is placed by being rotated from a position where the principal surface thereof is perpendicular to the propagation direction of the electromagnetic wave by a predetermined angle about a predetermined rotation axis not parallel to the polarization direction of the electromagnetic wave, such that when the void-arranged structure is projected onto a plane perpendicular to the propagation direction of the electromagnetic wave, one of the row and column directions of the void portions coincides with the polarization direction of the electromagnetic wave.

14. A measuring apparatus used in carrying out the measuring method according to claim 7, the apparatus comprising an electromagnetic-wave emitting unit that applies the first electromagnetic wave and the second electromagnetic wave having different polarization directions to the void-arranged structure.

15. The measuring apparatus according to claim 14, wherein the electromagnetic-wave emitting unit includes a polarization modulator capable of modulating a polarization state of the linearly polarized electromagnetic waves to two different polarization states for application of the first electromagnetic wave and the second electromagnetic wave.

16. A measuring apparatus used in carrying out the measuring method according to claim 11, the apparatus comprising a position control mechanism configured to control a position of the void-arranged structure.

17. The measuring apparatus according to claim 16, wherein the position control mechanism has a rotating function.

18. The measuring apparatus according to claim 16, comprising:

an electromagnetic-wave emitting unit that applies electromagnetic waves to the void-arranged structure on which the object is held; and a branching filter configured to separate the electromagnetic waves emitted from the electromagnetic-wave emitting unit into a first electromagnetic wave for obtaining the first frequency characteristic and a second electromagnetic wave for obtaining the second frequency characteristic.

19. The measuring apparatus according to claim 16, further comprising a plurality of light sources and/or a plurality of detectors.

20. The measuring apparatus according to claim 16, further comprising a plurality of detectors.

* * * * *